(12) United States Patent
Mikus et al.

(10) Patent No.: US 6,485,422 B1
(45) Date of Patent: *Nov. 26, 2002

(54) COMPUTER GUIDED CRYOSURGERY

(75) Inventors: Paul W. Mikus; Jay Eum, both of Irvine; Wilson S. Wong, Alhambra, all of CA (US)

(73) Assignee: Endocare, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/699,938

(22) Filed: Oct. 30, 2000

Related U.S. Application Data

(63) Continuation of application No. 09/318,710, filed on May 26, 1999, now Pat. No. 6,139,544.

(51) Int. Cl.$^7$ ................................................ A61B 8/00
(52) U.S. Cl. ......................................... 600/439; 606/21
(58) Field of Search ............................... 600/407, 437, 600/427, 411, 439, 459, 547, 3, 1, 461, 467, 462, 463; 606/21, 20, 23, 24–26, 130; 128/897, 920, 922–924

(56) References Cited

U.S. PATENT DOCUMENTS

| | | | |
|---|---|---|---|
| 4,672,963 A | 6/1987 | Barken | |
| 5,494,039 A | * 2/1996 | Onik et al. | 600/461 |
| 5,531,742 A | 7/1996 | Barken | |
| 5,647,868 A | 7/1997 | Chinn | 606/21 |
| 5,706,810 A | 1/1998 | Rubinsky et al. | |
| 5,882,306 A | 3/1999 | Ramamurthy et al. | 600/440 |
| 5,976,092 A | * 11/1999 | Chinn | 600/459 |
| 6,083,166 A | 7/2000 | Holdaway et al. | 600/439 |
| 6,095,975 A | * 8/2000 | Silvern | 128/922 |
| 6,129,670 A | * 10/2000 | Burdette et al. | 600/427 |
| 6,139,544 A | * 10/2000 | Mikus et al. | 600/439 |
| 6,190,378 B1 | * 2/2001 | Jarvinen | 606/20 |
| 6,235,018 B1 | * 5/2001 | LePivert | 600/547 |
| 6,248,101 B1 | * 6/2001 | Whitmore et al. | 606/1 |

FOREIGN PATENT DOCUMENTS

| WO | WO 98/23214 | 6/1998 |
|---|---|---|

* cited by examiner

*Primary Examiner*—Marvin M. Lateef
*Assistant Examiner*—Ali M. Imam

(57) ABSTRACT

A system for assisting surgeons in performing cryosurgery of the prostate by calculating optimal positions for cryoprobes and providing display based templates for overlay over an ultrasound image display, and displaying actual cryoprobes ultrasound images together with template images so that the surgeon may compare suggested and actual placement of the cryoprobes, and adjust placement accordingly.

11 Claims, 27 Drawing Sheets

COMPUTER GUIDED CRYOSURGERY

CROSS REFERENCE

This application is a continuation of U.S. application Ser. No. 09/318,710, U.S. Pat. No. 6,139,544 filed May 26, 1999.

FIELD OF THE INVENTIONS

The inventions described herein relate to the field of cryosurgery and ablative surgery.

BACKGROUND OF THE INVENTIONS

The system and methods described below enhance the accuracy and effectiveness of cryosurgery of the prostate. Cryosurgery of the prostate is an effective treatment for prostate cancer and benign prostate hyperplasia, conditions which affect many men.

The use of cryosurgical probes for cryoablation of the prostate is described in Onik, *Ultrasound-Guided Cryosurgery, Scientific American* at 62 (January 1996) and Onik, Cohen, et al., *Transrectal Ultrasound-Guided Percutaneous Radial Cryosurgical Ablation Of The Prostate*, 72 Cancer 1291 (1993). In this procedure, generally referred to as cryoablation of the prostate, several cryosurgical probes are inserted through the skin in the perineal area (between the scrotum and the anus) which provides the easiest access to the prostate. The probes are pushed into the prostate gland through previously placed cannulas. Placement of the probes within the prostate gland is visualized with an ultrasound imaging probe placed in the rectum. The probes are quickly cooled to temperatures typically below −120° C. The prostate tissue is killed by the freezing, and any tumor or cancer within the prostate is also killed. The body will absorb some of the dead tissue over a period of several weeks. Other necrosed tissue may slough off through the urethra. The urethra, bladder neck sphincter and external sphincter are protected from freezing by a warming catheter placed in the urethra and continuously flushed with warm saline to keep the urethra from freezing.

To maximize the effectiveness of the procedure, the entire prostate should be ablated. At the same time, surrounding structures such as the rectum and the neurovascular bundles should not be frozen. The amount of the prostate which is ablated by the cryosurgical procedure depends on the number of cryoprobes used and their placement within the prostate gland. Wong, et al., Cryosurgery as a Treatment for Prostate Carcinoma, 79 Cancer 963 (March 1997), suggests a placement scheme for cryosurgical probes within the prostate. Probes were inserted through the perineal area into the prostate while attempting to keep the probes within 1.8 cm of each other. The systems and methods presented below were developed to assist surgeons in placing the probes as suggested by Wong, or as suggested by others, with the assistance of ultrasound imaging, computer graphics, and computer assisted calculations of optimal probe placement within the prostate.

SUMMARY

The inventions described below are designed to assist surgeons performing cryoablation of the prostate gland in a male human patient. The system includes an ultrasound imaging probe and associated image processing hardware and software and image display systems, a computer system which generates a user interface which accepts input from a surgeon as to the size and shape of the prostate gland imaged by the ultrasound imaging system, and calculates an optimal cryosurgical probe placement for the particular imaged prostate gland, and displays a template on the display screen indicating the optimal placement. The system also images the cryosurgical probes as they are inserted into the prostate gland, and presents the images of the cryosurgical probes on the display for comparison with the template and the optimal placement positions as calculated by the system. Using the system, the surgeon performing the procedure can be assured that the intended probe placement corresponds to optimal positions, and that the actual probe placement is accomplished according to the optimal placement.

Also described are algorithms and a corresponding computer program designed to calculate the optimal position of the cryoprobes for effective cryosurgical ablation of the prostate in a wide range of patients. The algorithms decide whether the prostate size fits within parameters for successful calculations, whether five or six probes are required, the optimal placement for two cryoprobes in the anterior lobe of the prostate gland, the optimum placement for two cryoprobes in the outer portions of the posterior lobe of the prostate, and the optimum placement for one or two cryoprobes in the center area of the posterior lobe of the prostate.

BRIEF DESCRIPTION OF THE DRAWINGS

FIG. 28 is a copy of the portion of the computer program which performs the calculations used to determine the optimum placement of cryoprobes.

DETAILED DESCRIPTION OF THE INVENTIONS

Figure 1:
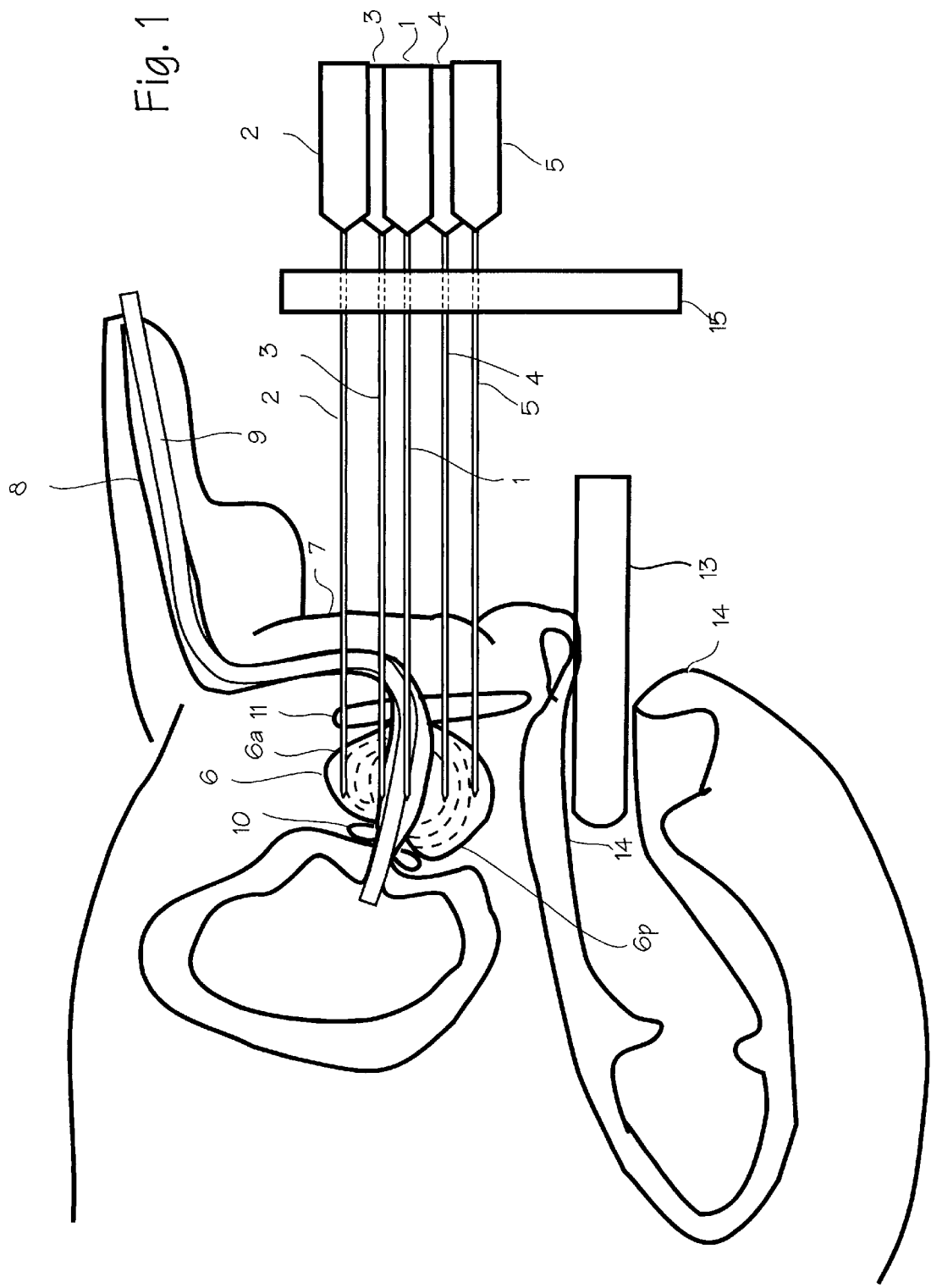
FIG. 1 is an overview of the transperineal cryosurgical ablation of the prostate.

FIG. 1 shows one of the basic operations for which the cryoprobes are designed. Several probes 1, 2, 3, 4 and 5 are shown inserted in the prostate 6 (in some instances a sixth probe, not shown, is used). All five probes are inserted through the perineal region 7 between the scrotum and the anus. Probes 2 and 3 are shown inserted into the anterior lobe 6a of the prostate, and Probes 1, 4 and 5 are shown inserted into the posterior lobe 6p, which is larger than the anterior lobe. The probes are placed within the prostate according to procedures well known in the art, and a suitable procedure is described in step-by-step detail in Onik, et al., *Percutaneous Prostate Cryoablation*, (1995) at pages 108–112 and Onik, *Ultrasound-Guided Cryosurgery*, Scientific American at 62 (January 1996). Typically five or six probes are used in the procedure, though more or less may be used when required by unusual anatomy of a particular patient. The urethra 8 which passes through the prostate is one of the anatomic structures that usually should not be frozen during this surgery. Accordingly, the urethra is protected and kept warm with the urethral warming catheter 9. The bladder neck sphincter 10 and the external sphincter 11 are also structures that should be protected from freezing, and these are protected from freezing by the warming catheter. Neurovascular bundles on the right and left of the prostate should also be protected from freezing. Transrectal probe 13 is inserted into the rectum 14 in order to visualize the placement of the probes and the growth of the iceballs formed by the cryoprobes. To assist in placement of the cryosurgical probes, a template 15 is used which supports the probes during insertion and while they are installed in the body. The patient is placed horizontally on an operating table with legs positioned to provide access for the ultrasound probe to be inserted into the rectum and cryoprobes to be inserted through the perineal area into the prostate.

The transrectal ultrasound probe 13 is used to visualize the prostate and the cryosurgical probes. The ultrasound probe operates in the range of about 2–10 MHz, depending on the equipment used (the process described herein may be used with any ultrasound probe and ultrasound generator, which may be selected based on various technical, medical and budgetary considerations). The image is displayed as a two dimensional representation of the boundaries of the prostate, as illustrated in FIGS. 2 and 3.

Figure 2:
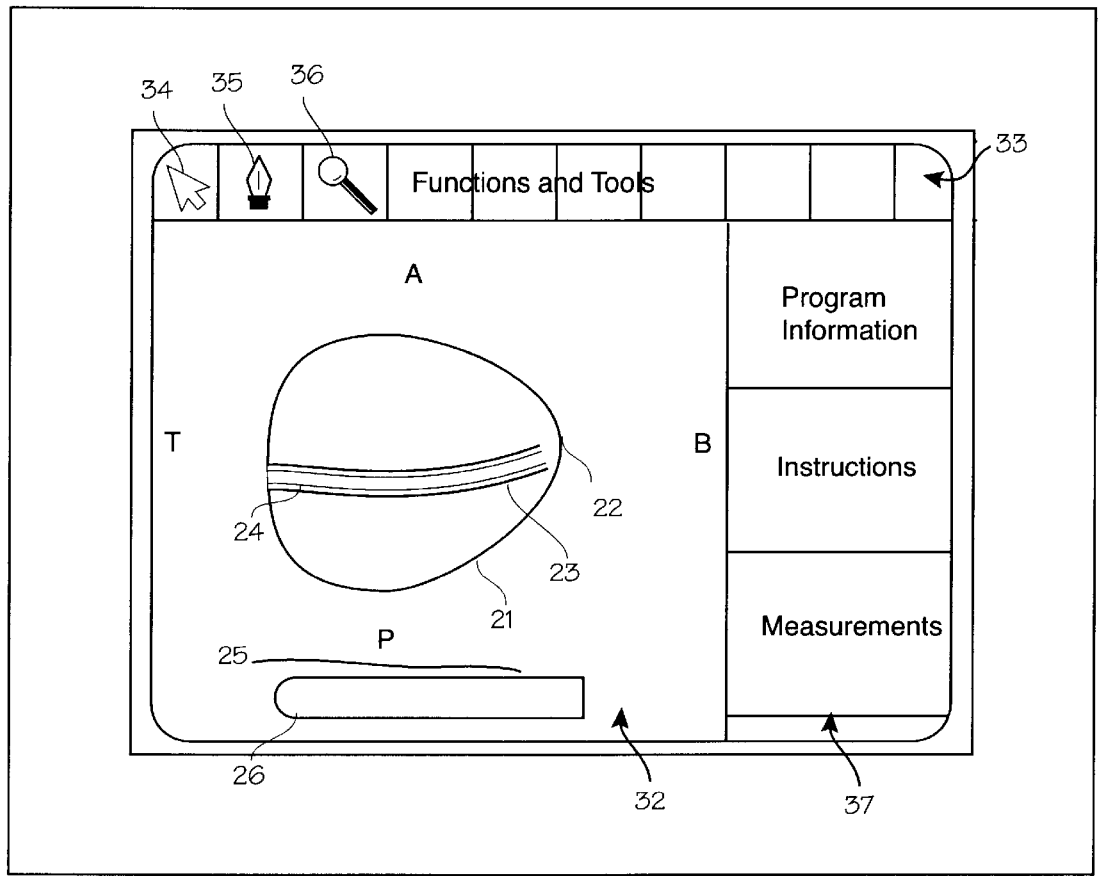
FIG. 2 is an illustration of a sagittal or longitudinal cross section of the prostate and surrounding anatomy as displayed on the video display provided by the system.

FIG. 2 shows a longitudinal (also referred to as sagittal or coronal) cross section of the prostate, generally denoted by the ultrasound outline 21. The top, bottom, anterior and posterior sides of the outline are delineated by the letters T, B, A and P, respectively. The apex of the prostate 22 points generally to the perineal area shown in FIG. 1. Other anatomical structures visible in display include the urethra, whose outline 23 may not appear fully in the coronal cross section. The urethral warming catheter image 24 appears within the urethra. Also, the ultrasound image of the rectal wall 25 appears along the bottom of the display area, and the image of the ultrasound probe 26 may appear directly below the rectal wall. The rectum and rectal wall are preferably straightened by the pressure exerted by the insertion of the ultrasound probe, as explained below, to set up the system for the calculations and displays described below. Since the prostate is generally oblong in this direction, and longer in this direction than in the horizontal or transverse cross section, we refer to this cross section as the longitudinal cross section.

Figure 3:
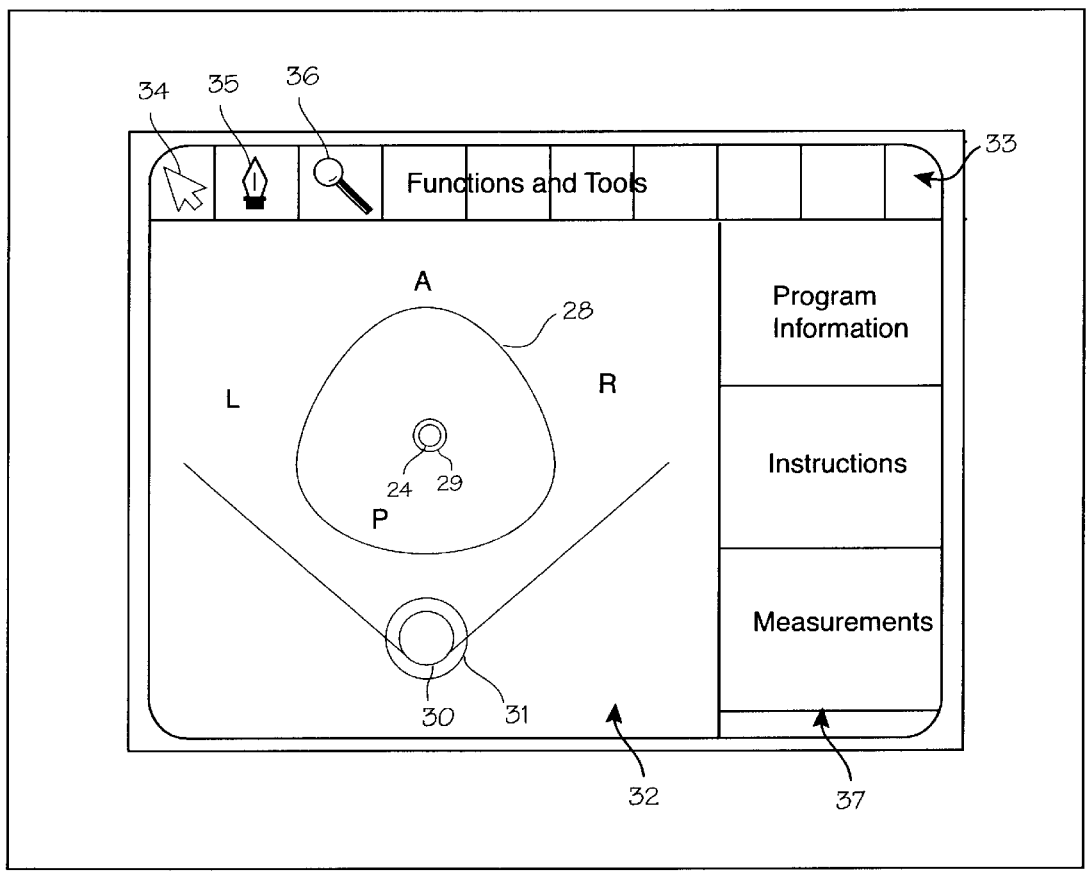
FIG. 3 is an illustration of a horizontal or transverse cross section of the prostate and surrounding anatomy as displayed on the video display provided by the system.

FIG. 3 shows a horizontal or transverse cross section of the prostate generally denoted by the ultrasound outline 28. The anterior (towards the front of the body), posterior (toward the back), right and left of the prostate are marked as A, P, R and L, respectively. The urethra appears as the ultrasound outline 29. The warming catheter outline 24 appears within the urethra image 29. Also visualized in the display is the shadow of the probe itself, marked as item 30, and the ultrasound outline of the rectum 31. The image shown is refreshed at a regular rate by the ultrasound imaging system and the images may shift with movement of the ultrasound probe. The surgeon is instructed to translate the ultrasound probe within the rectum to obtain several cross sectional views and to choose the largest viewable cross section of the prostate for analysis and display.

Other aspects of the display shown in FIGS. 2 and 3 are provided as part of the user interface. The ultrasound display area 32 is used by the system to display the image of the prostate generated by the ultrasound imaging system, and is used as described below to enter information regarding the prostate outline and display suggested probe placements. The toolbar area 33 across the top of the screen is used by the system to present drawing and viewing tools and other interface tools (typical selection, pen and zoom tool icons 34, 35 and 36 are illustrated in the toolbar). The data presentation area 37 along the right side of the screen is used by the system to indicate program information and patient information, step by step instructions to the surgeon, and measurements derived from operator inputs in the display area.

The system provides a function for the operator to freeze the image in order to accept outlining and path-finding inputs followed by calculating functions. The operator is prompted to orient the ultrasound image such that the rectal wall is substantially parallel to the bottom edge of the display area. The operator is instructed or prompted to search for the largest cross section of the prostate as seen through the ultrasound probe, and to freeze the image on the screen. In response to the operator's instruction to the system to freeze the images, a single frame will be captured or grabbed by the system software and displayed as a frozen image. The frozen images are presented on the display to allow the operator to interact with the system to determine the size and shape of the prostate.

Figure 4:
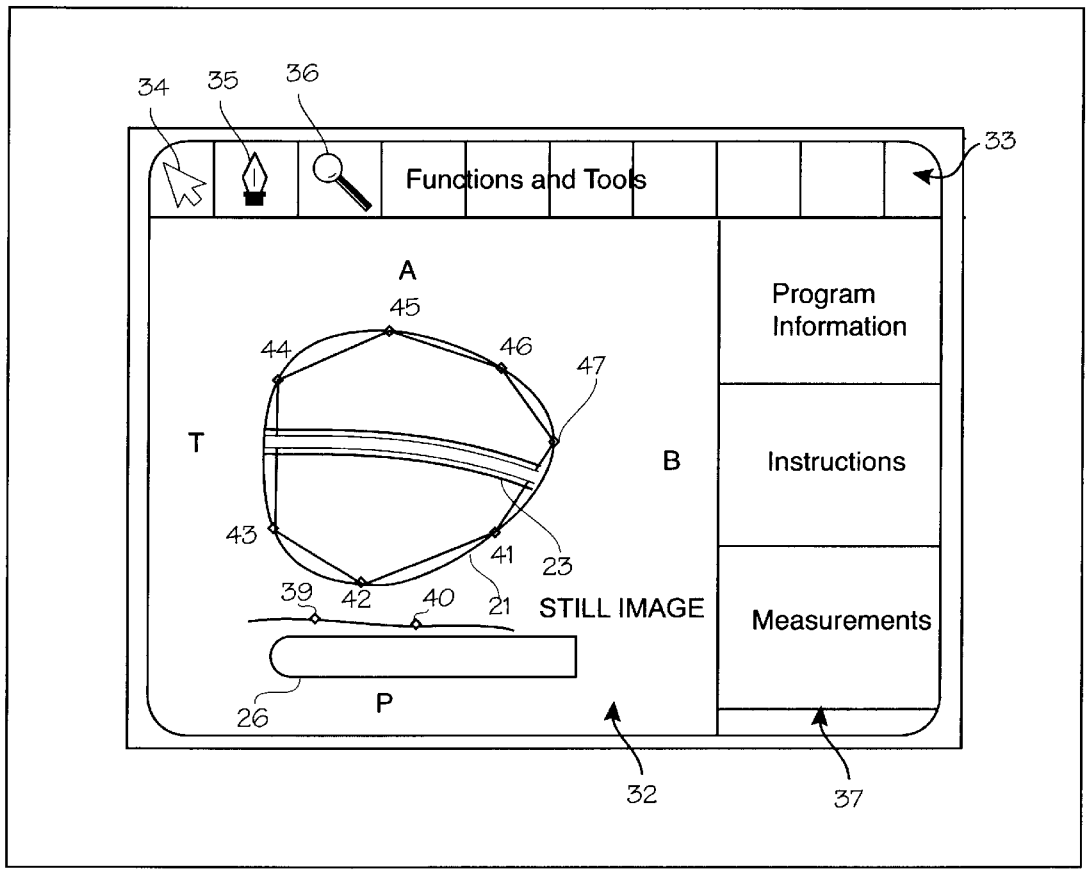
FIG. 4 is an illustration of the system in use to outline the prostate image shown in FIG. 2.

FIG. 4 shows the grabbed image of the coronal cross section of the prostate shown in FIG. 2. First viewing the live image of FIG. 2 to inspect a number of cross sections along different planes, the surgeon instructs the system to freeze the image when an appropriate cross section is displayed. Generally, the largest visualized cross section in which the urethra appears should be used. Visualization of the urethra indicates that the image plan is at or near the center of the prostate. When instructed do so, the computer system grabs a frame from the live image, and presents a frozen image as illustrated in FIG. 4.

To determine if the cross section is acceptable and that the ultrasound probe is placed in the preferred position, the operator marks at least two points 39 and 40 along the rectal wall image 25 and instructs the computer system to analyze these two points to make sure that they are sufficiently horizontal (parallel with the ultrasound probe) and straight to support later functions of the system. If the rectal wall image is not horizontal within acceptable limits (currently, not more than 4 mm difference in height on the display area), and near the bottom of the display area within acceptable limits (currently set at 3 cm), the system will reject the frozen image as a basis for later functions and prompt the operator to correct the image orientation, probe placement or patient position. If the rectal wall image is substantially horizontal on the display, indicating that the rectal wall is parallel with the ultrasound probe, the system will indicate that the image is acceptable and prompt the operator to continue the procedure and outline the prostate image on the display.

Using outline functions of the supporting computer system, such as the pen tool selected from the toolbar, the operator outlines the image of the prostate by moving the pen tool around the outline and anchoring the pen tool at selected points around the perimeter until the prostate is fully outlined. (The anchor points may be created by the operator with standard input devices such as a mouse or touch screen and other standard software tools such as an anchor point adding tool, pen tool or polygon tool.) The operator then creates an outline of the coronal cross section of the prostate by drawing a polygon having several anchor points 41, 42, 43, 44, 45, 46, and 47 around the perimeter of the prostate ultrasound image 21 (any number of anchor points may be used). The operator indicates to the system that the outline is accurate relative to the displayed image, and the computer system accepts the image as a representation of the coronal cross section of the prostate.

Figure 5:
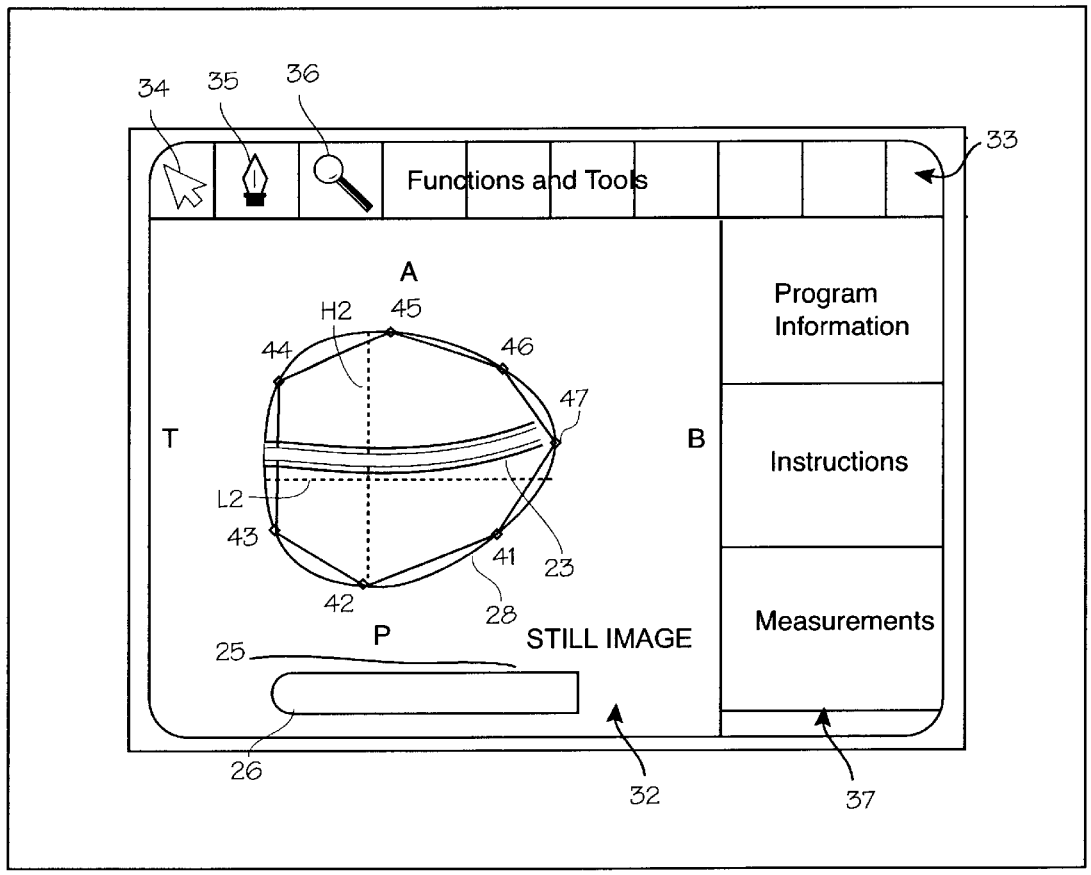
FIG. 5 is an illustration of the system in use to outline the prostate image shown in FIG. 2, illustrating measurements calculated by the computer system.

Referring to FIG. 5, the computer system searches the display data for the outline and defines the two parameters H2 and L2. The parameter H2 is the "height" of the prostate that will be considered by the system. The parameter L2 is the length of the prostate that will be considered by the program. (It should be appreciated that any variable name may be assigned to these parameters; the H2 and L2 designations correspond to variables used in the computer program which the inventors have devised to implement the system.) At this point, the computer system analyzes the variables to assist the operator in deciding how to accomplish the cryosurgery. If L2 is greater than 35 mm, the system will notify the operator that a pullback freeze is required to completely ablate the prostate. The doctor will then be apprised that a single freezing operation will be insufficient, and that the cryosurgery must be accomplished in two steps, with a first freeze being accomplished with the probe tips near the top of the prostate and the second freeze be accomplished afterward, with the cryoprobes pulled back about 10 mm toward the apex of the prostate. If H2 is less than a predetermined distance from either end of the prostate, the system will prompt the operator to verify that the outline accurately reflects the size and shape of the prostate, whereupon the process may continue or be restarted.

Figure 6:
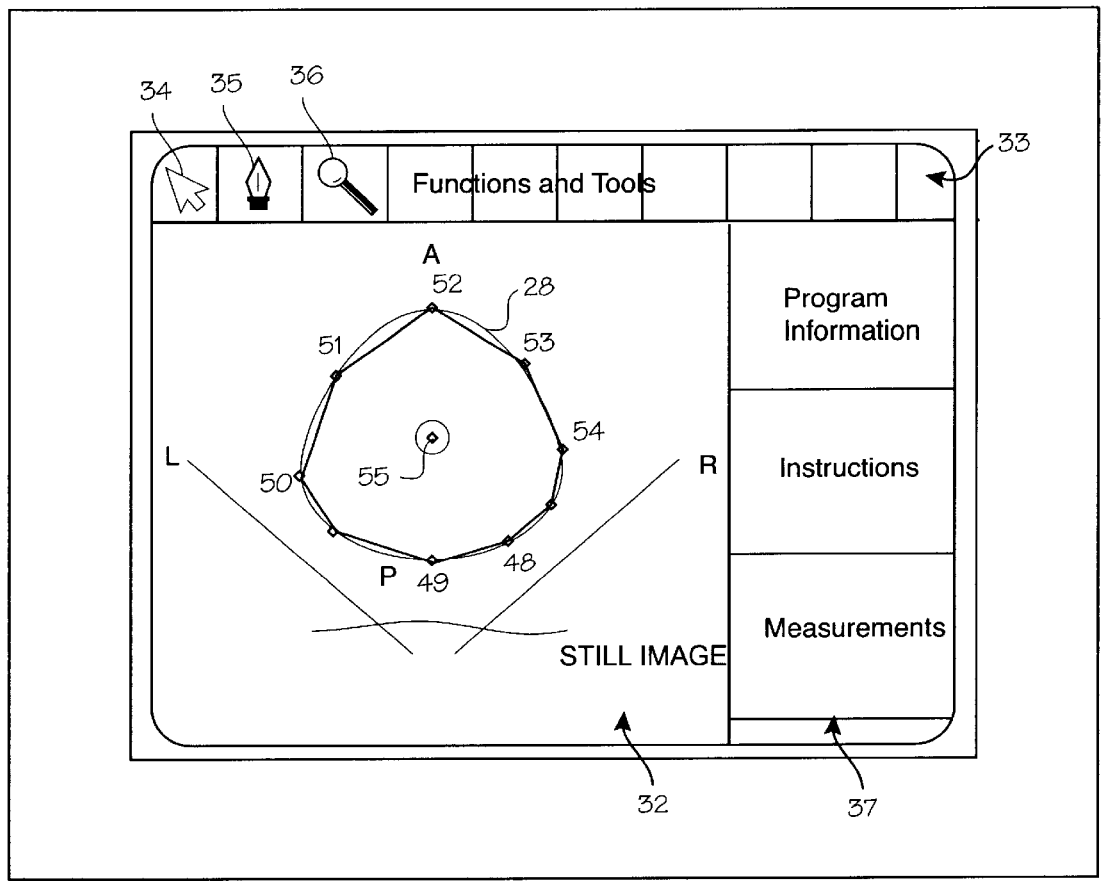
FIG. 6 is an illustration of the system in use to outline the prostate image shown in FIG. 3.

Next, the operator performs the outlining task in relation to the horizontal cross section. Thus, FIG. 6 shows the display of FIG. 3 modified by the operator with the addition of a polygon comprising several anchor points 48, 49, 50, 51, 52, 53 and 54 around the perimeter of the prostate ultrasound image 28 (any number of points may be entered). The operator indicates to the system that the outline is accurate relative to the displayed image, and the computer system accepts the image as a representation of the coronal cross section of the prostate. The operator is also prompted to mark the center of the urethral prostate, and enters a mark 55, which the computer system accepts as the location of the prostatic urethra in the horizontal cross section.

Figure 7:
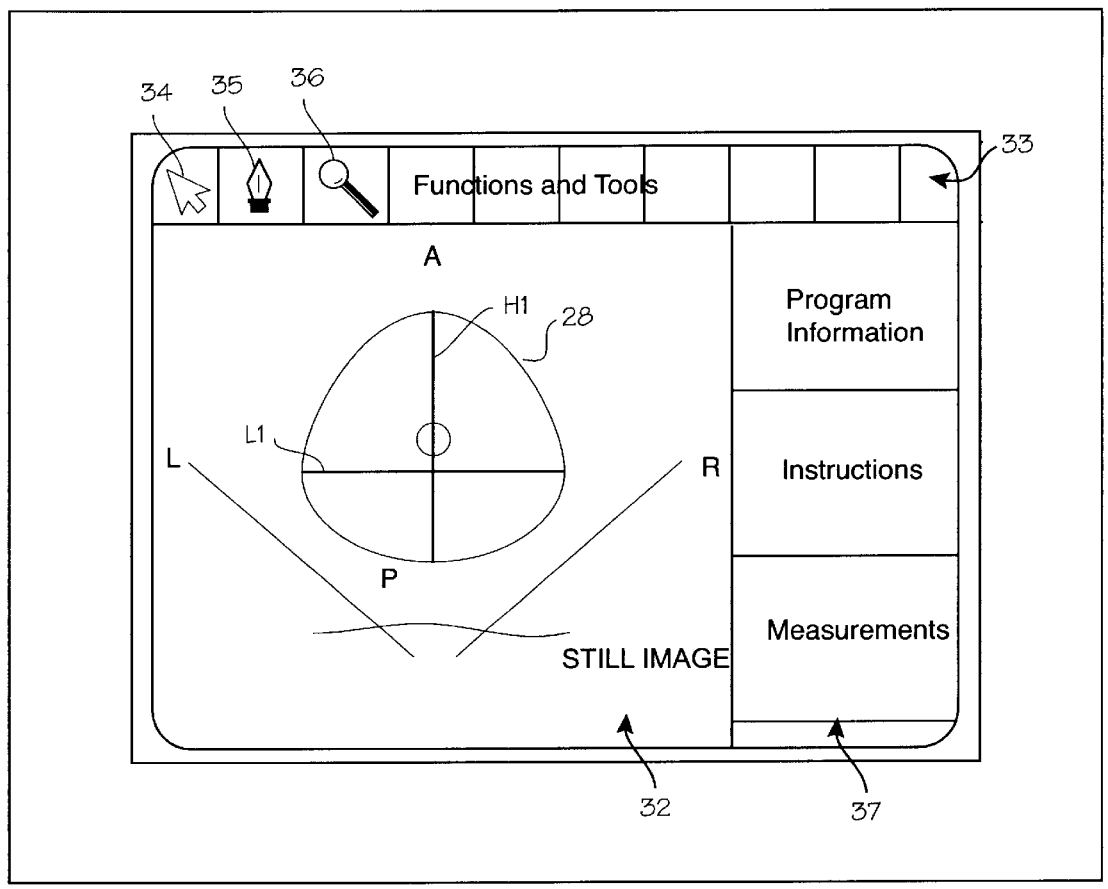
FIG. 7 is an illustration of the system in use to outline the prostate image shown in FIG. 3, illustrating measurements calculated by the computer system.

As shown in FIG. 7, the computer system searches the display data for the outline and defines the two parameters H1 and L1. The parameter H1 is the "height" of the prostate that will be considered by the system, as determined in the horizontal cross section image. The parameter L1 is the width of the prostate that will be considered by the program. After the parameter H1 is determined, the computer system will compare it with the parameter H2 (the height as determined in the coronal cross section image as shown in FIG. 5). These two parameter are expected to be the same if the operator has actually selected the largest identifiable cross section in both planes. If H1 is different from H2 by more that a predetermined amount, this indicates that the cross sections do not closely correspond to the largest actual cross section, and the computer system will prompt the operator to restart the procedure at the image selection stage (presently, 3 mm difference is the maximum allowed difference, but this may vary with experience with the present system, or with the cryoprobes in use). Upon determining L1, the computer will compare it with a predetermined width, and if L1 is greater than the predetermined width (currently set at 3.5 cm) the system will notify the operator that six cryoprobes are required for the operation, and proceed as described below to calculate a position for the sixth cryoprobes.

The system will not calculate positions for extremely large or small glands, thus if the prostate width in the anterior lobe is greater than 54 mm, the system will display a message in the instruction area that the gland is too large for calculated positioning of the probes. If the prostate width in the anterior lobe is smaller than 23 mm, the system will display a message in the instructions area that the gland is too small for calculated positioning of the probes.

The supporting computer system is programmed with software which permits the drawing and outlining functions described above, and calculation functions for calculating the size of the prostate based on the input, determining the optimal number of probes required, and determining the optimal placement for the probes. When the outline of the prostate has been entered into the computer system, and the computer system has checked that the various parameters are within predetermined ranges, the computer system operates to calculate the optimum number of cryoprobes and the optimum placement of the cryoprobes, and communicate this information to the operator.

The computer system requires input or calculation of certain parameters in order to determine probe placement. The parameters required are:

H1: Maximum front to back thickness in the horizontal cross section;

L1: Maximum right to left thickness in the horizontal cross section;

H2: Maximum front to back thickness in the sagittal cross section;

L2: Maximum right to left thickness in the sagittal cross section;

prtUrethra: The location of the center of urethra within the horizontal cross section;

iY0: the vertical position of the anterior extreme of the prostate gland in the horizontal cross section;

iY01 and iY5: The vertical position of the rectal wall in the horizontal cross section, as approximated by the posterior extreme of the prostate gland;

The measured parameters are used to calculate the optimum position for the placement of the cryosurgical probes. The optimum placement of probes is determined empirically, based upon histological evidence of lethal ablation zones, and the calculations may vary as histological data accumulates. The system first calculates the position of probes in the horizontal plane, and from this derives the position of the probes in the coronal cross section.

Figure 8:
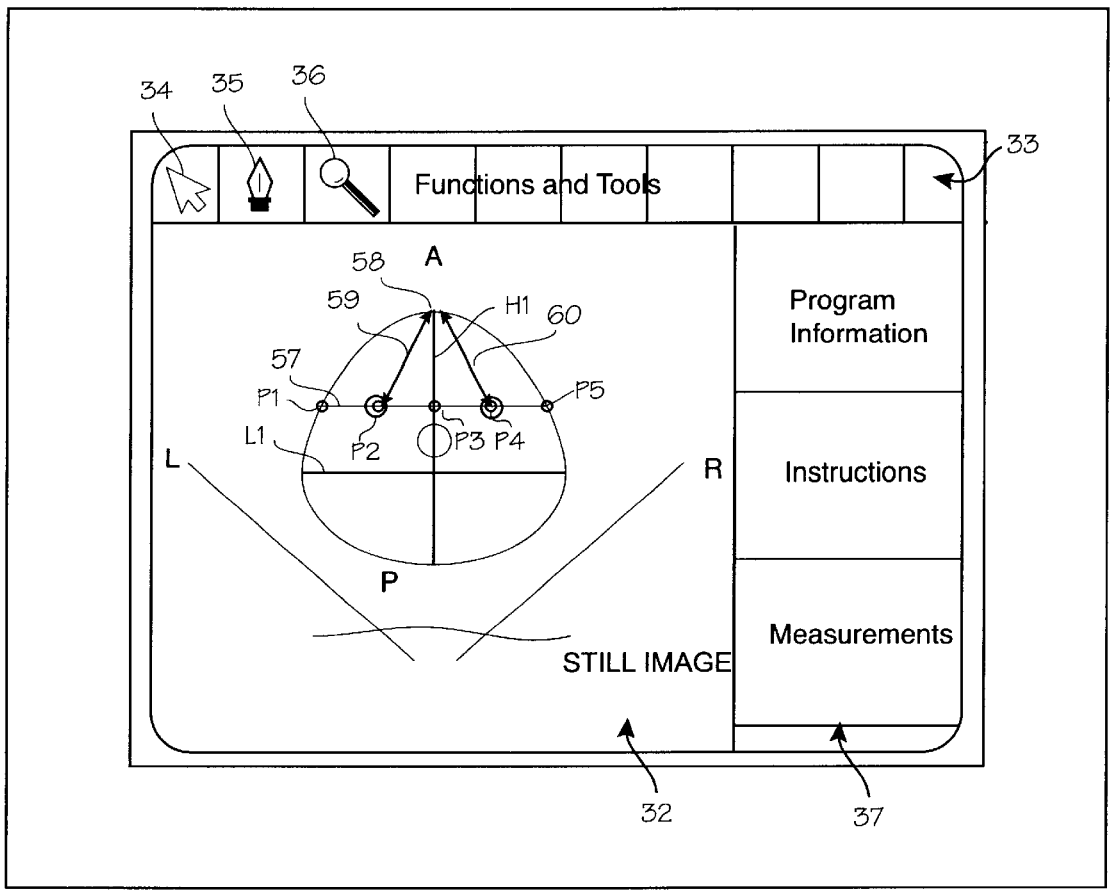
FIG. 8 is an illustration of the system determination of the optimum placement of cryoprobes within the anterior lobe of the prostate image shown in FIG. 3, where the prostate is relatively large.
Figure 9:
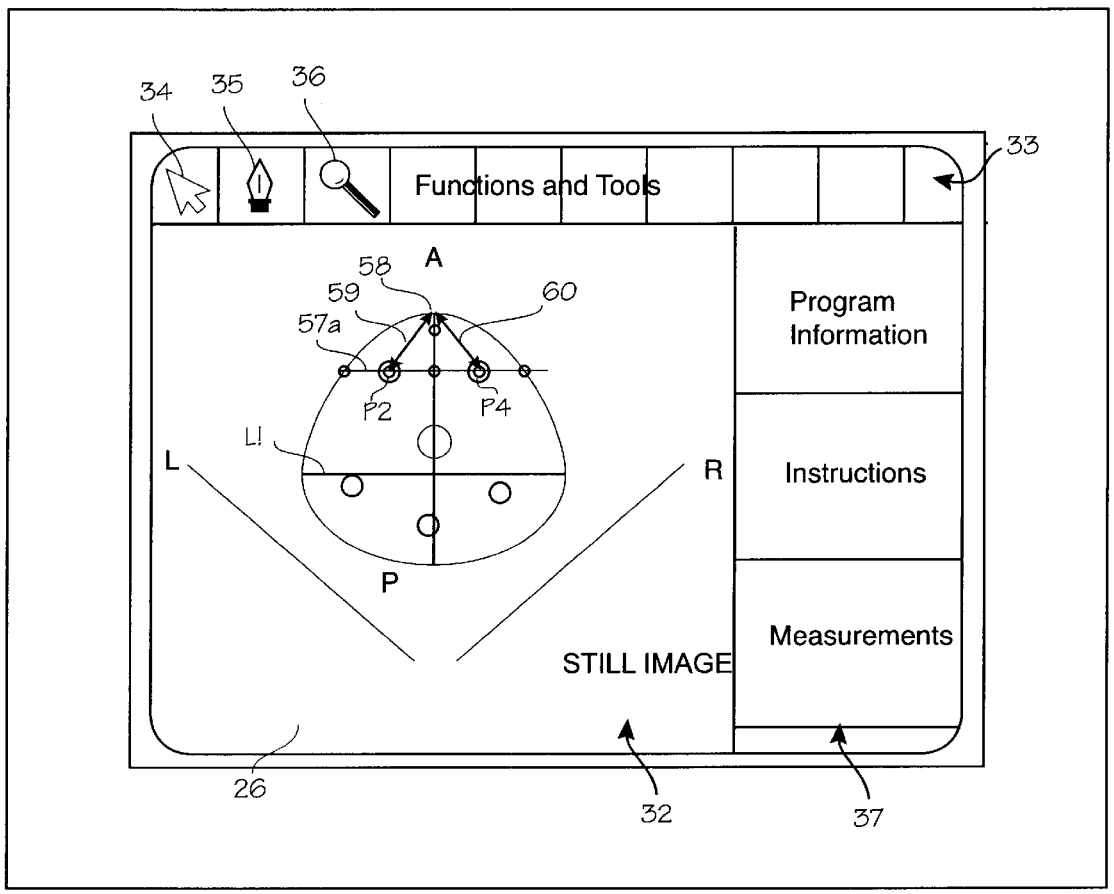
FIG. 9 is an illustration of the system determination of the optimum placement of two cryoprobes within the anterior lobe of the prostate image shown in FIG. 3, where the prostate is relatively large.

Using data from the outlining step, the system first calculates the desired position of probes 2 and 3, which are placed in the anterior lobe of the prostate. Referring to FIG. 8 (horizontal cross section), if L1 exceeds 3.6 cm, the computer system searches the horizontal outline of the prostate (using a line by line measurement of the display data generated by the computer system) from the top to identify the first horizontal length which equals 3.6 cm. When this line is found, as exemplified by line 57, the line is divided into four sections of equal length, and the five points P1, P2, P3, P4, and P5. The system next tests whether the distance from point P2 to the midline highest point 58 (pctrpt) is less than 9 mm. If this distance is less than 9 mm, the system uses this vertical position for placement of the probes 2 and 3. Graphical markers corresponding to Probes 2 and 3 are placed on the points P2 and P4, which correspond to the middle points on the two line segments from the outer edge of the prostate to the center of the prostate at the point where the width of the prostate first measures 3.6 cm. If this distance is initially more than 9 mm, the system moves the line 57 upward until the distance is 9 mm, and adjusts P1 through P5 to match the outer edge of the prostate, the centerline of the prostate, and the points between the center and the outer edges, and uses this new vertical position for placement of probes 2 and 3. This is illustrated in FIG. 9, where line 57a has been raised to a higher level in the display so that distances 59 and 60 are 9 mm. Graphical markers corresponding to Probes 2 and 3 are placed on the points P2 and P4, which now correspond to the middle points on the two line segments from the outer edge of the prostate to the center of the prostate at the point where the width of the prostate first measures 3.6 cm, after this line segment has been raised to the point where the middle points are 9 mm from the centerline front of the prostate. Thus, in the case where the prostate width is greater than 3.5 cm, the first two graphical marker probes are placed by the system on the display in optimal position.

Figure 10:
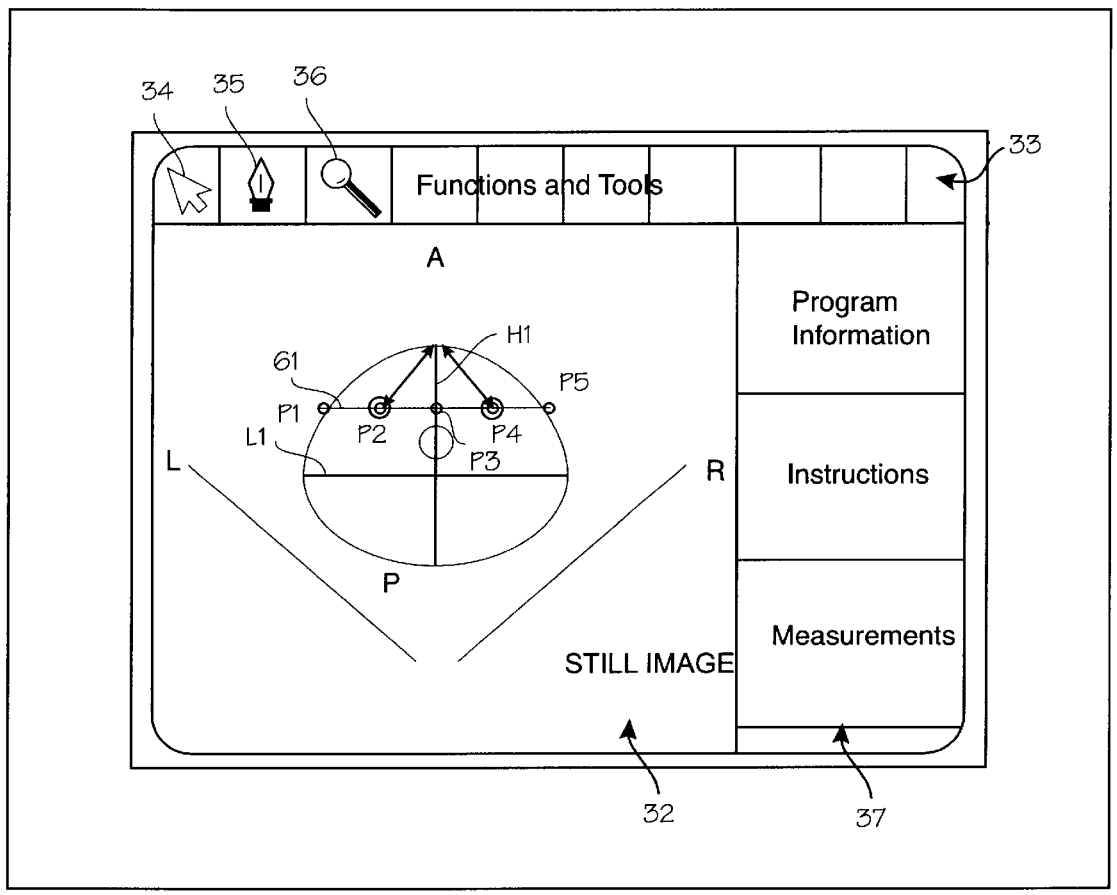
FIG. 10 is an illustration of the system determination of the optimum placement of two cryoprobes within the anterior lobe of the prostate image shown in FIG. 3 where the prostate is relatively small.

In the case that L1 is less than 3.5 cm, placement of the first two probes is determined as illustrated in FIG. 10. The computer system searches the horizontal outline of the prostate (using a line by line measurement of the display data generated by the computer system) by iteratively drawing horizontal lines and identifying the five points P1 through P5, from the top to identify the first horizontal line in which the distance point P2 to the top centerline is 9 mm, or until the distance between P2 and P4 is 9 mm, whichever occurs first. When this line is found, as exemplified by line 61, the points P2 and P4 are identified as the position for Probes 2 and 3, respectively.

Figure 11:
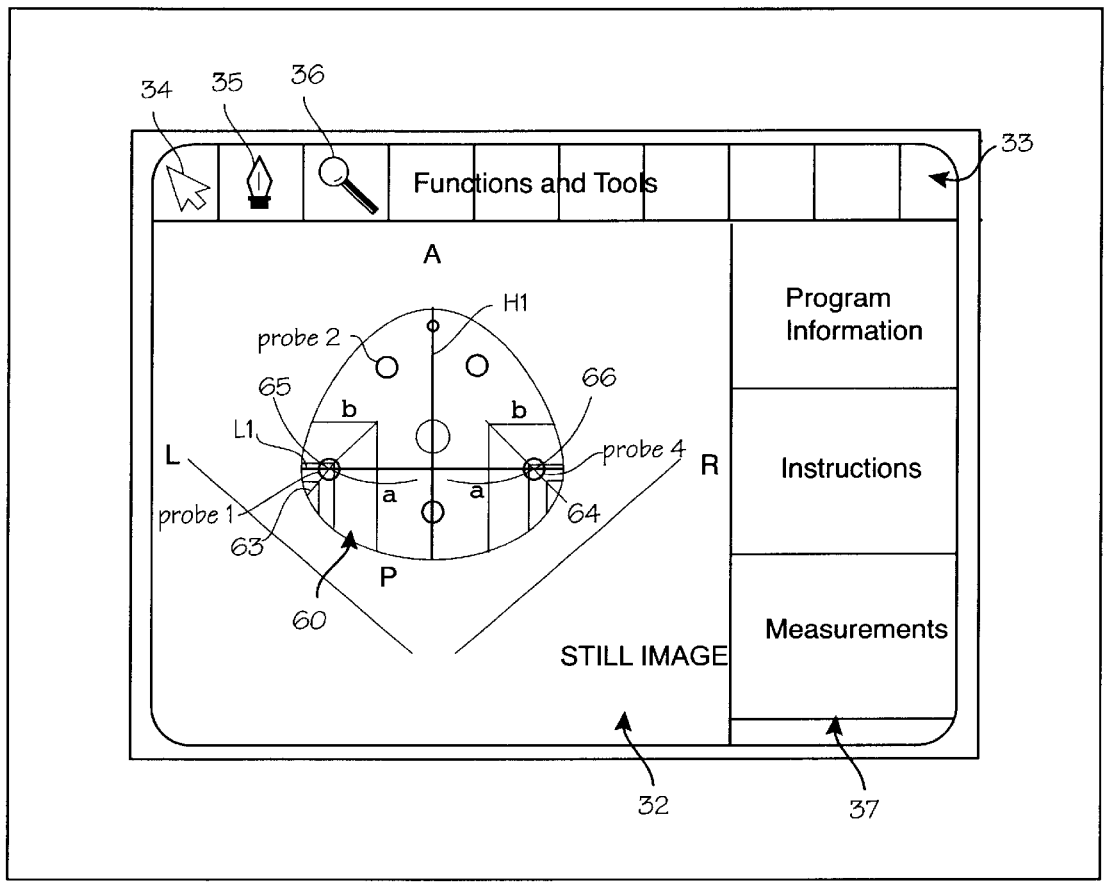
FIG. 11 is an illustration of the system determination of the optimum placement of two cryoprobes within the posterior lobe of the prostate image shown in FIG. 3.

With the positions for Probes 2 and 3 determined, the system next determines the optimal position for probes 1 and 4, which are placed in the posterior lobe of the prostate. The procedure is explained in reference to FIG. 11. The system finds all points at which the distance along the horizontal from the outer edge of the prostate (distance b) is one half of the distance along the vertical from the outer edge of the prostate (distance a). All the points along lines 63 and 64 (both representing line b=1/2a on opposite sides of the prostate) illustrated in FIG. 11 fit this criterion (note that the line is not necessarily straight, since it is defined in reference to the irregular outline of the prostate). The system next draws the arc 65 at a distance of 18 mm from point Probe 2, and a similar arc 66 from point Probe 3. The point where the arc 65 and the line 63 intersect is chosen as the position of probe 1 and the point where the arc 66 and the line 64 intersect is chosen as the position of probe 4. Currently, these probes are positioned in this manner regardless of prostate size, except as inherited from the positioning of probes 2 and 3.

Figure 12:
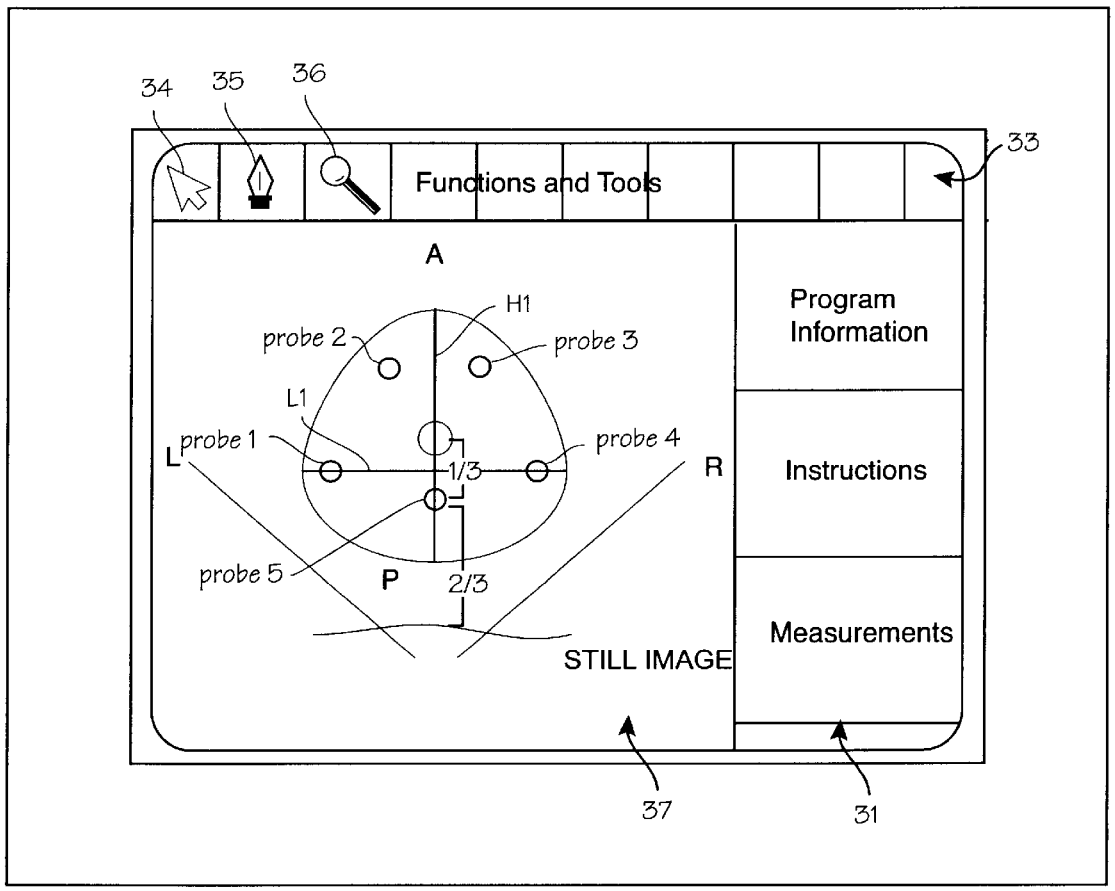
FIG. 12 is an illustration of the system determination of the optimum placement of a fifth cryoprobes within the prostate image shown in FIG. 3, in the case that only five probes are required for effective cryosurgical ablation of the prostate.
Figure 13:
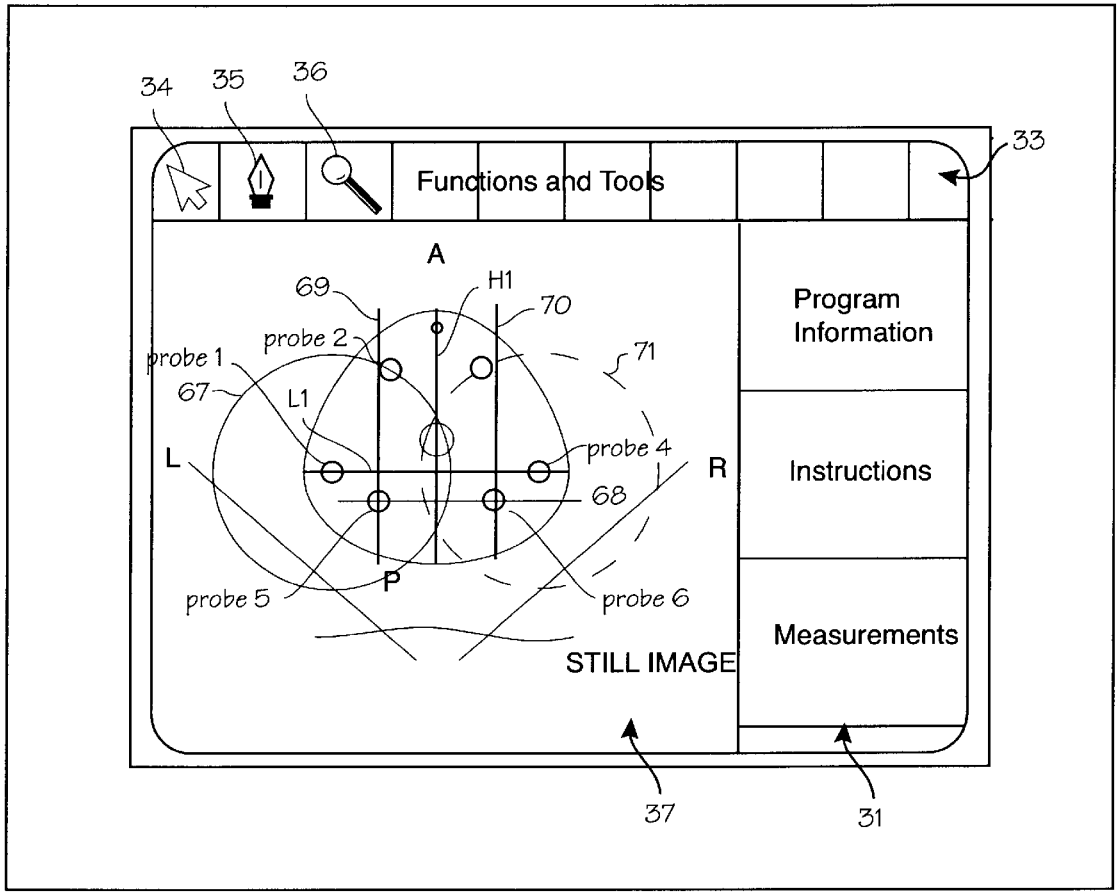
FIG. 13 is an illustration of the system determination of the optimum placement of the fifth and sixth cryoprobes within the prostate image shown in FIG. 3, in the case that a sixth probe is required for effective cryosurgical ablation of the prostate.

Placement of probe 5 depends on the size of the prostate. If the system has decided that 5 probes are sufficient to accomplish effective ablation, the fifth probe is placed on the line H1 between the rectal wall and the urethra. The system finds the point along H1 which is 2/3 of the way up from the rectal wall, and assigns this position to Probe 5, as illustrated in FIG. 12. If the system has decided that 6 probes are necessary (i.e., L1 is greater than 3.6 cm), the system determines the position of probes 5 and 6. As illustrated in FIG. 13, the system determines the position of these probes relative to previously placed probes. The system determines the position of probe 5 so that it falls within 1.8 cm of probe 1, and the distance from the horizontal centerline L1 to the probe is not more than 1 cm, and the distance between from the vertical center line H1 is not more than 9 mm. Arc 67 is drawn around Probe 1 with radius of 18 mm, and a line 68 is drawn 1 cm below L1. Probe 5 is placed on the higher of (1) the intersection of line 69 (drawn 9 mm away from H1) with the arc 67, or (2) the intersection of the line 69 and line 68. A similar construction is performed on the other side of the prostate, and probe 6 is placed within the intersection of line 70 and the arc 71 or the line 68, whichever is higher. Thus Probes 5 and 6 are located on the screen relative to the ultrasound image of the prostate.

Figure 14:
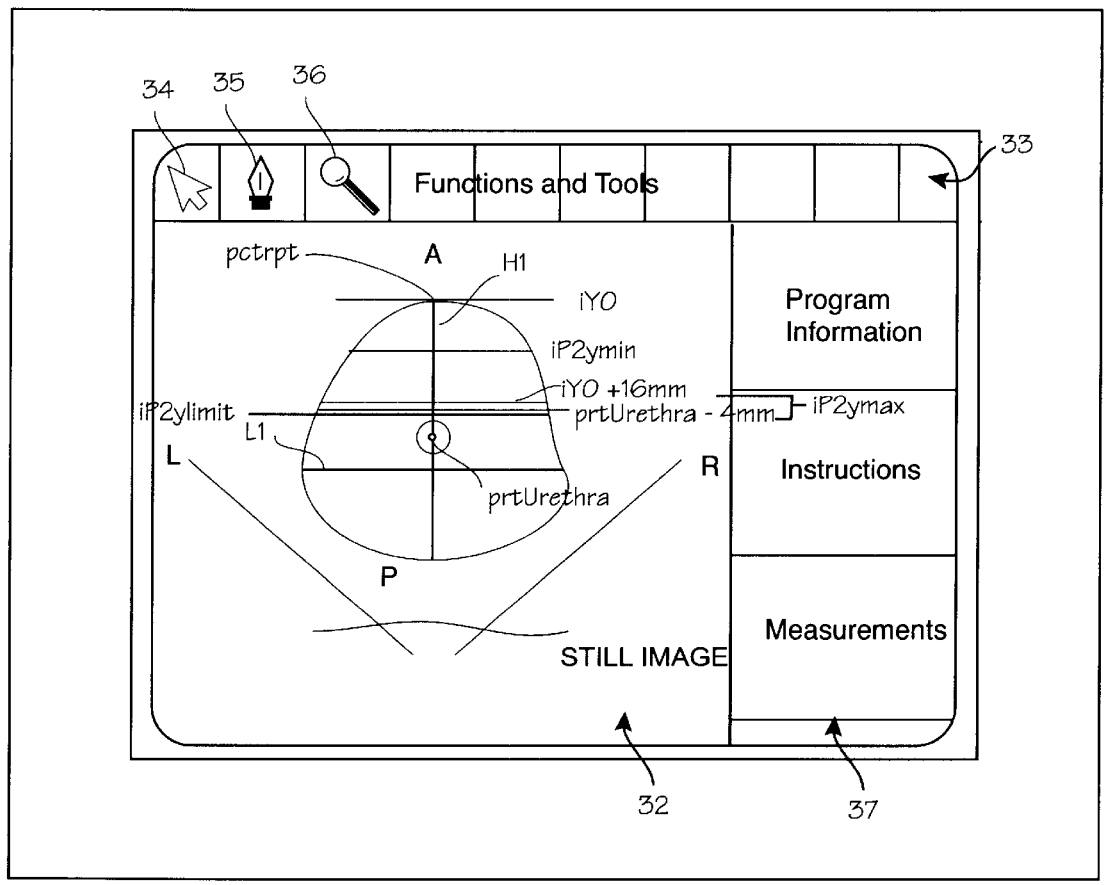
FIGS. 14 through 21 illustrate a second method for the system determination of the optimum placement of cryoprobes within the prostate.

FIGS. 14 through 21 illustrate a second method for the system determination of the optimum placement of cryoprobes within the prostate. Referring to FIG. 14, the prostate outline is used as before to define H1 and L1. The system finds the top of the prostate outline, and sets the variable iY0 at the top of prostate (represented by the horizontal line iY0), and sets the variable pctrpt as the x and y values at the top of the prostate. Minimum and maximum potential vertical levels are defined for analysis as locations for probes 2 and 3. The system defines the variable ip2ymin at 8 mm below the line iY0 (labeled as horizontal line ip2ymin), and defines the variable ip2ymax at highest of (1) 16 mm below iY0 (labeled as horizontal line iY0+16 mm) and (2) 4 mm above the center of the urethra (labeled as horizontal line pctUrethra-4 mm), and defines the variable ip2ylimit (the lowest allowed height for probes 2 and 3) as the horizontal line 7/16 down H1 (labeled iP2ylimit). The system searches line on the screen starting at ip2ymin and continuing through to the highest of ip2ymax or ip2ylimit, which ever is higher. (If iP2ymin is lower than iP2ymax, the system sets ip2ymin as the y value for probes 2 and 3.)

Figure 15:
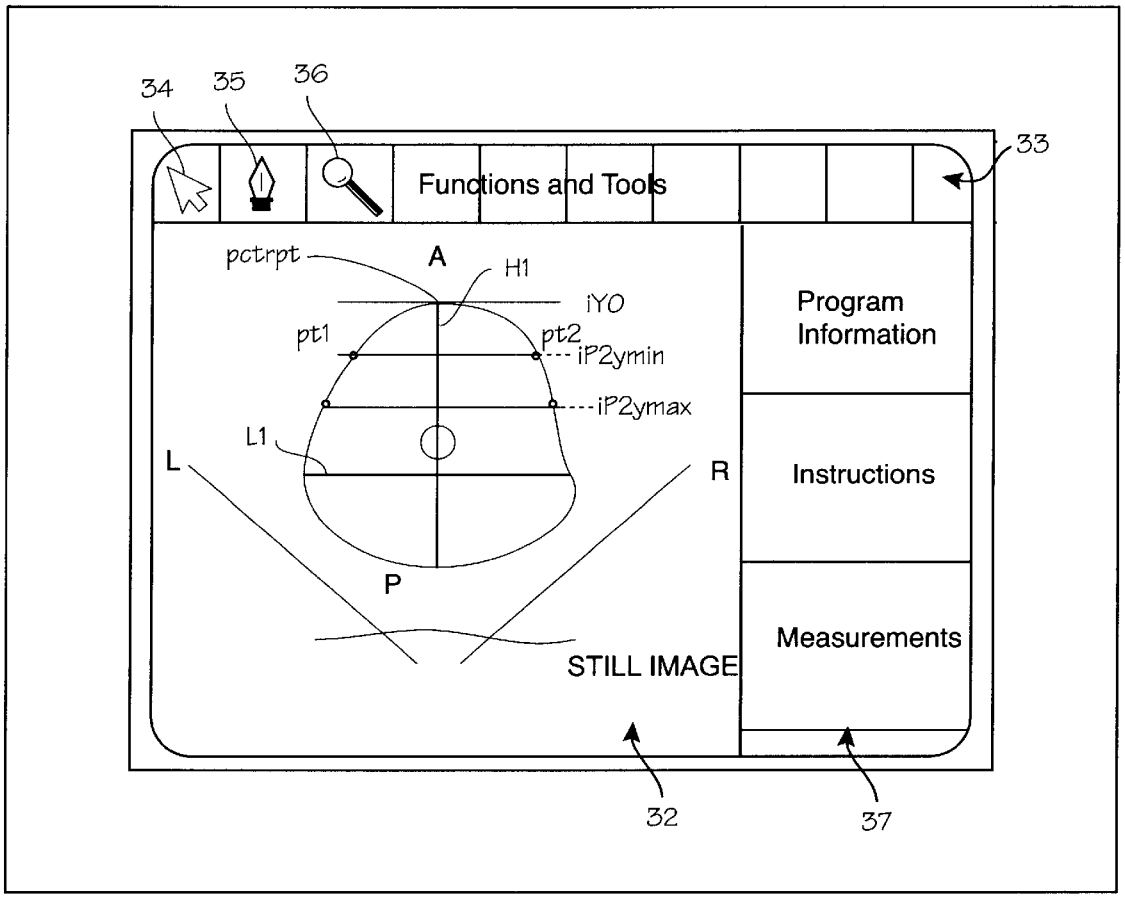

Referring now to FIG. 15, the system searches the region defined in FIG. 14 for the desired vertical placement of probes 2 and 3. The system determines the length of ip2ymin, and the length of line ip2ymax across the prostate. If upper line (iP2ymin) length (dpt1topt2min) is greater than 54 mm, the outline cannot be automatically analyzed because it is too big, and the system communicates this to the operator. If the lower line (iP2ymax) length (dpt1topt2max) is smaller than 23 mm, the outline cannot be automatically analyzed because it is too small, and the system communicates this to the operator. In all other instances, the system continues on to create and define variables as follows:

For L1 between 26 and 36 mm, create variable pt1topt2, and store the minimum value of 26 or dpt1topt2max (length of ip2ymax line) as pt1topt2;

For L1 between 36 and 54 mm, store the minimum of 36 or dpt1topt2max (length of line iP2ymax) as pt1topt2;

For L1 between 54 nd 58 mm, store the minimum of 44 or dpt1topt2max as pt1topt2;

For L1 greater than 58 mm, store the minimum of 54 or dpt1topt2max as pt1topt2.

Figure 16:
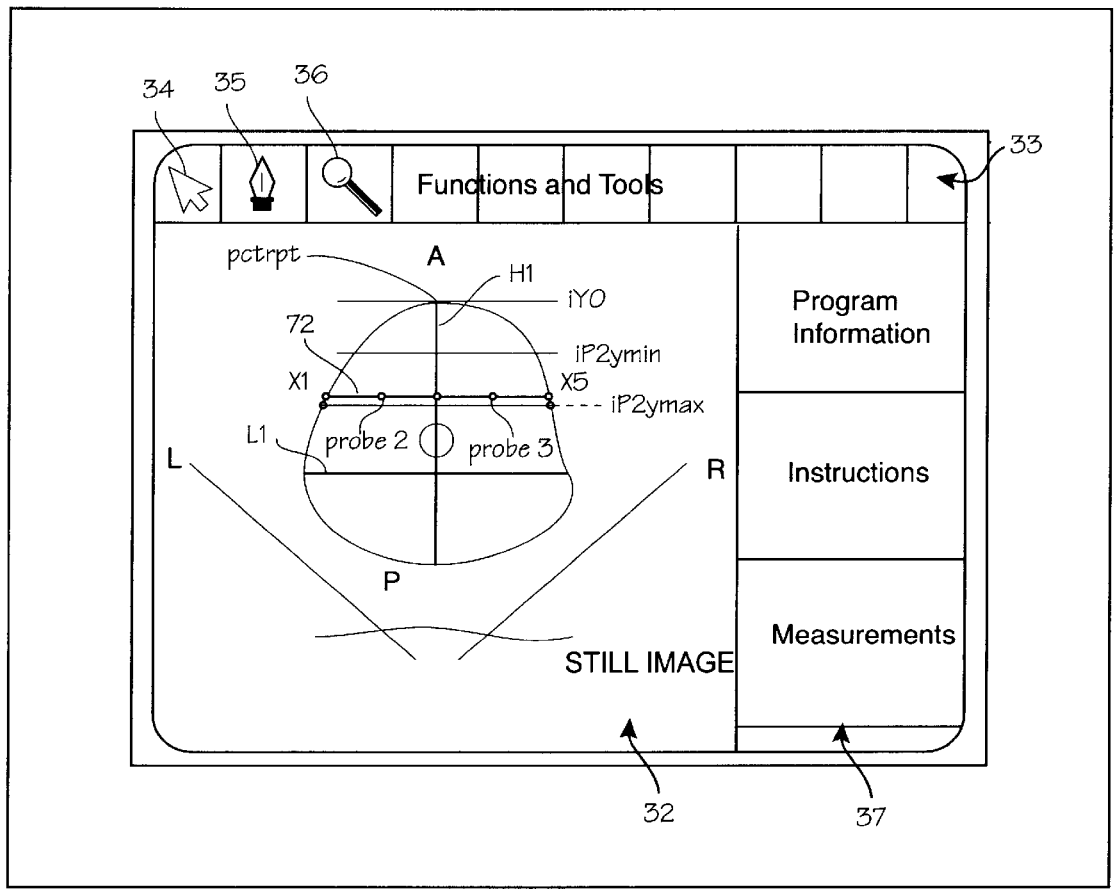

Now referring to FIG. 16, the system searches for the proper height for probes 2 and 3. From the top line (iP2ymin), the system scans each pixel line from iP2ymin to iP2ymax, searching for outside points X1 and X5 on the outline intersecting the horizontal line. When a line is found where the length of this line equals the defined dPt1toPt2 (calculated in reference to FIG. 15, above), that line is used as the vertical placement of probes 2 and 3. The corresponding line in FIG. 16 is labeled 72. Finally, the system calculates the x values for probes 2 and 3, setting them along the line at a spacing of 1/4 and 3/4 from the left, respectively. Thus, the system determines the position of two probes in the anterior lobe of the prostate based upon the width of the prostate approximately at the anterior-most location of (1) 16 mm posterior to the anterior extremity of the prostate, (2) 4 mm anterior to the center of the prostatic urethra, or (3) 7/16 of the total thickness of the prostate from the anterior extremity of the prostate.

Figure 17:
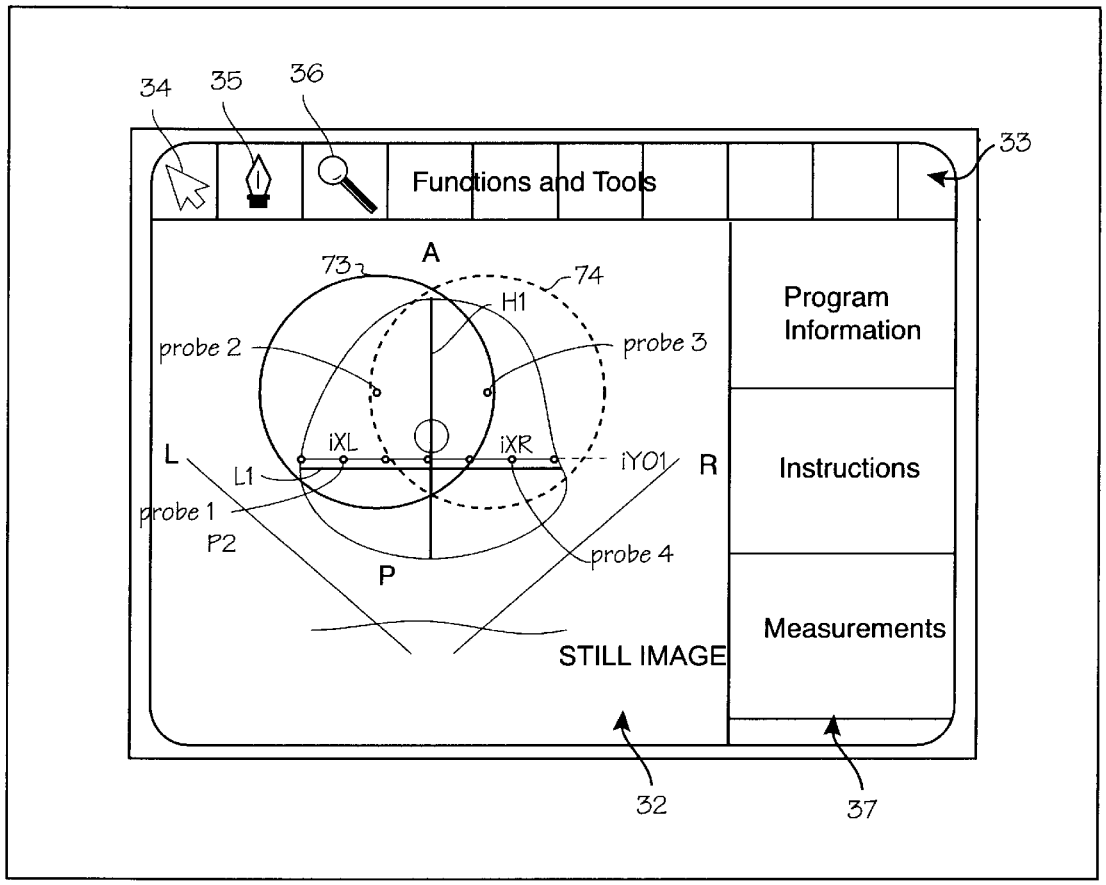
Figure 18:
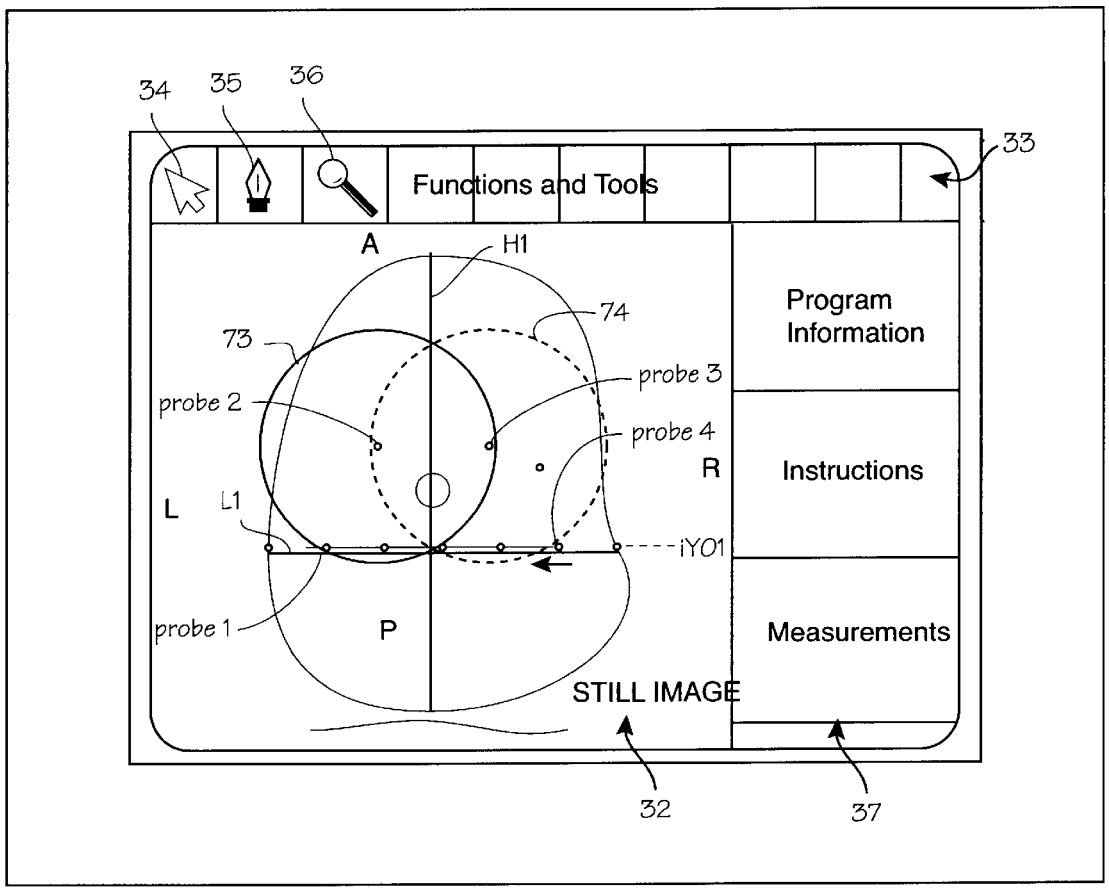

Now referring to FIG. 17, the system analyzes the outline to determine the proper location of probes 1 and 4 in the posterior lobe of the prostate. The system defines the vertical location iY01 (horizontal line iY01 in FIG. 17) as the y value or line at 5/8 down the prostate (5/8 down the length of H1). The system determines the Y distance between iY01 line and probes 2 and 3 (about 10 mm, as illustrated). If this distance is less than 16 mm, the system uses iY01 line as vertical height for placement of probes 1 and 4. Here, iY01 is only 10 mm away, so this is the height for probes 1 and 4. If the distance is greater than 16 mm, the system raises line iY01 until it is only 16 mm down from probes 2 and 3. To determine the horizontal placement of probes 1 and 4, the system places point iXL 1/6 across iY01 line, and if greater than 18 mm from probe 2, slide right (or left) until the point is 18 mm from probe 2 (i.e., within circle 73, drawn at a radius of 18 mm from probe 2). Similarly, the system places point iXR 5/6 of the distance across the line iY01, and if greater than 18 mm from probe 3, the point is moved left (or right) until the point is 18 mm from probe 3 (i.e., within circle 74, drawn at a radius of 18 mm from probe 3). As illustrated, both points fall within 18 mm of the probe above, so points iXL and iXR are used as the points for suggested placement of probes 1 and 4 respectively. FIG. 18 illustrates the same procedure in relation to a larger prostate which requires sliding point iXR to the left after initial placement at 5/6 across line iY01, so that it comes within 18 mm of probe 3 (and meets circle 74). In all other respects, FIG. 18 is described in the same manner as FIG. 17. Thus, the system determines the position of two probes in the posterior lobe of the prostate based upon the width of the prostate at the anterior-most location of (1) approximately 5/8 of the total thickness of the prostate from the anterior extremity of the prostate or (2) 16 mm posterior to the two probes positioned in the anterior lobe of the prostate.

Figure 19:
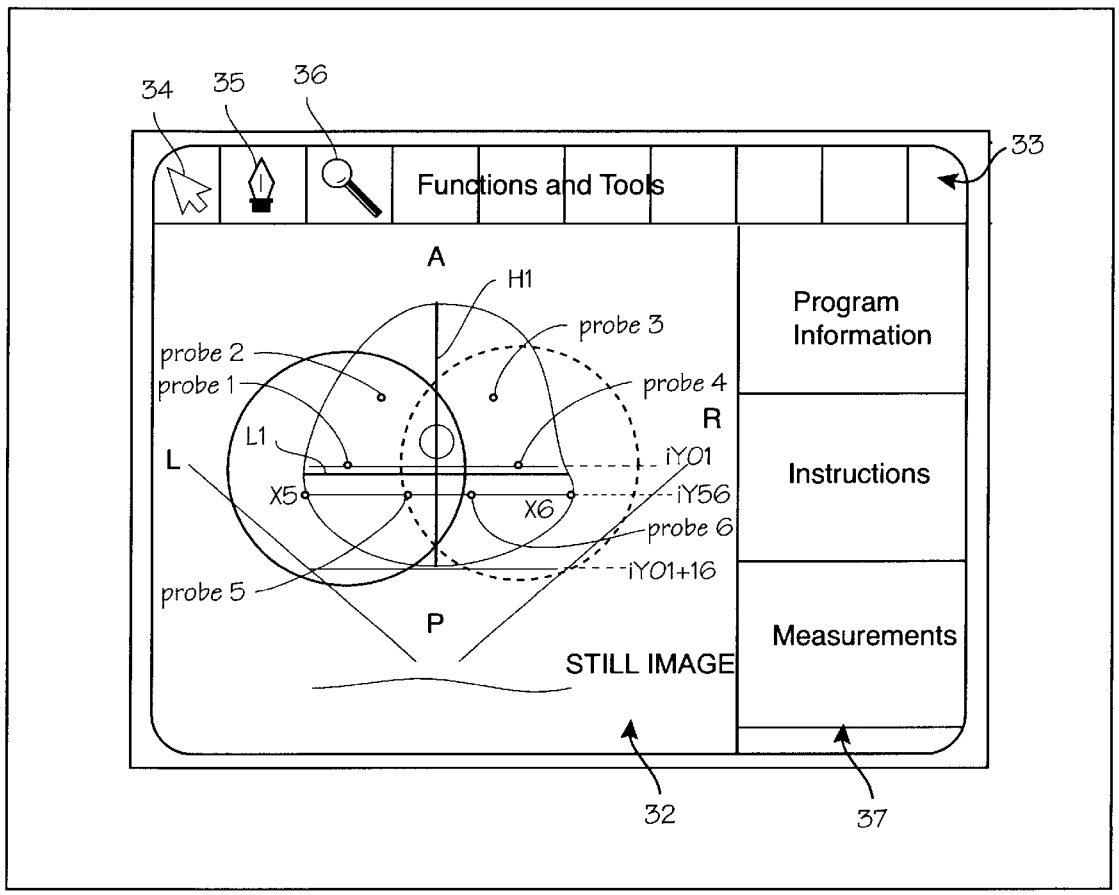
Figure 20:
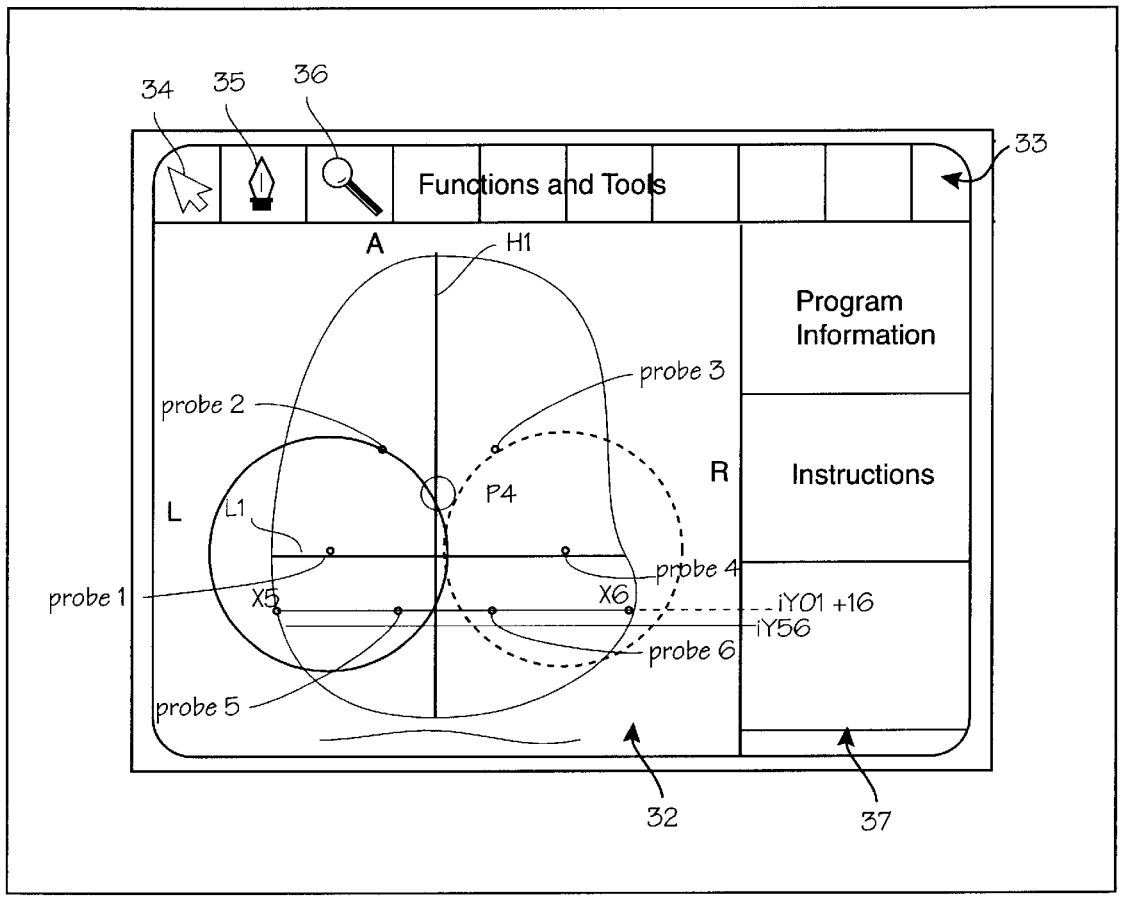

Next, the system determines the placement of Probes 5 and 6 within the posterior lobe of the prostate. Referring to FIG. 19, the system sets line iY01 as y height of probes 1 and 4, and sets the horizontal line iY56 at 1/4 up from bottom of screen (prostate/rectum/screen bottom are in reality so close together that they may be treated as the same y level), and sets the line (labeled as the horizontal line iY01+16) 16 mm down from probes 1 and 4. Then, the system resets line iY56 at the highest (the minimum y value) of the two lines, here the 1/4 up line is chosen. The system places points X5 and X6 at left and right extremities of line iY56, which is the intersection of the prostate outline with iY56. To place the probes 5 and 6 at the appropriate horizontal location, the system moves points X5 and X6 inward toward H1 until they are 10 mm apart. FIG. 20 illustrates the placement of probes 5 and 6 in a larger prostate, to illustrate the system choice of the highest line for placement of the probes. Here, line iY56 is below line iY01+16, so line iY56 is reset to the height of line iY01+16. Once again, the points X5 and X6 are moved inward along the higher line until they are only 10 mm apart, and probes 5 and 6 are located at these points, as illustrated in the figure. Thus the system determines the position of the two probes 5 and 6 in the center portion of the posterior lobe of the prostate based upon the width of the prostate at a the anterior-most location of (1) approximately 1/4 of the distance on the display from the rectum to the top of the display; (2) 16 mm posterior to the two probes 1 and 4 already positioned in the posterior lobe of the prostate.

Figure 21:
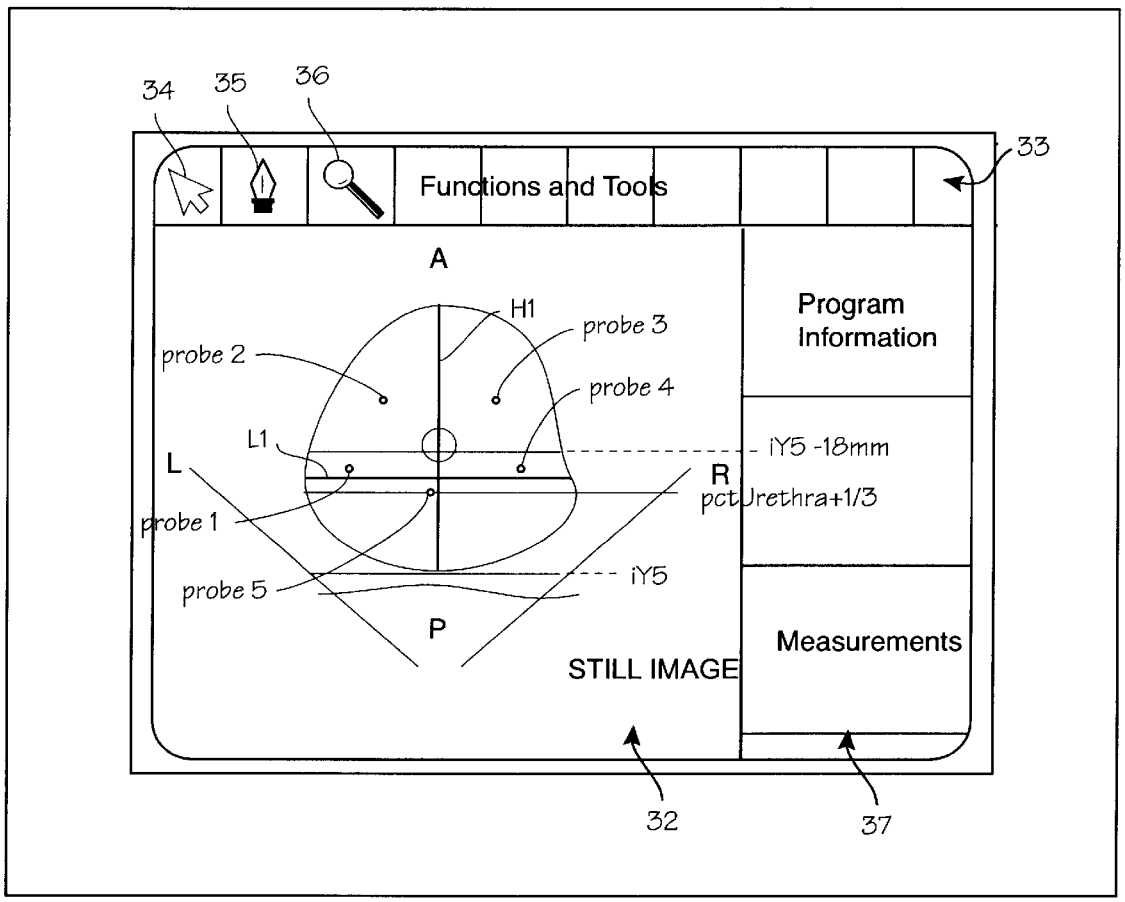
Figure 22:
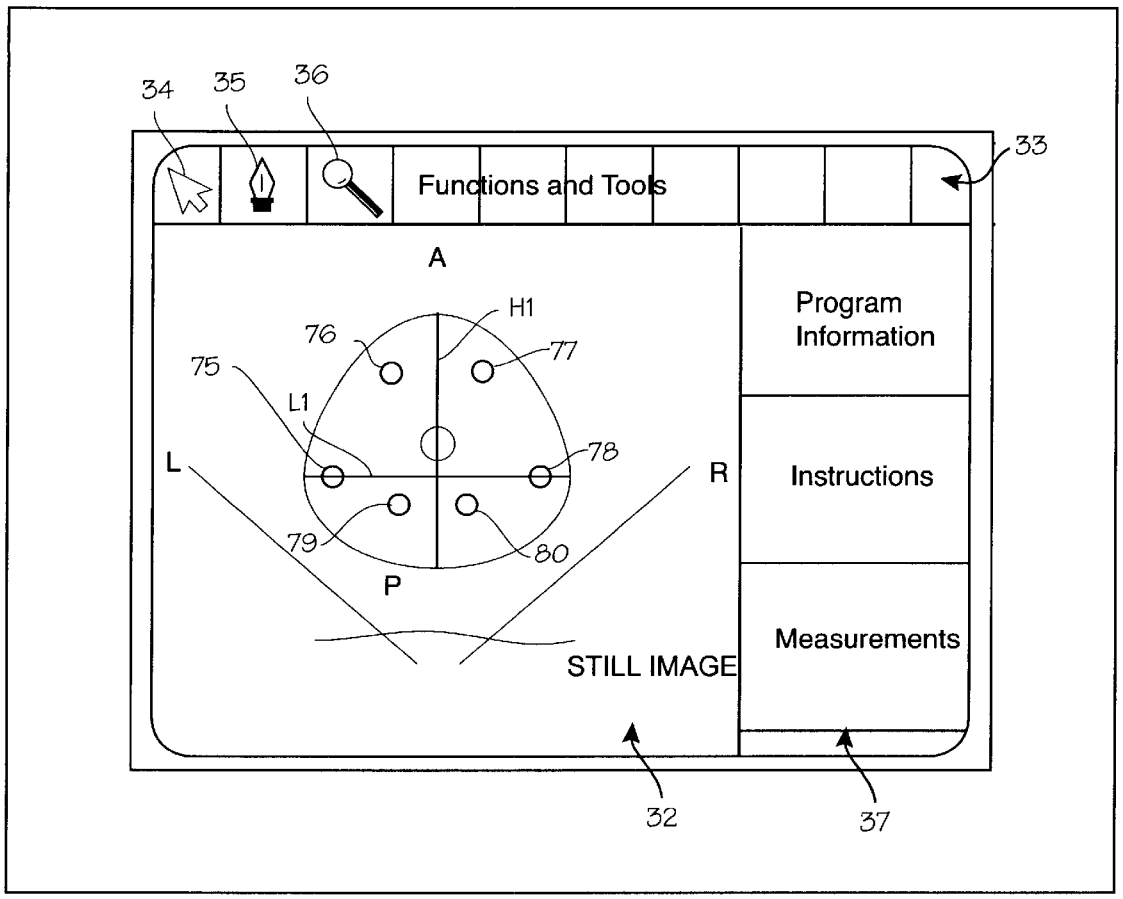
FIG. 22 is an illustration of the system output indicating the optimum placement of the fifth and sixth cryoprobes within the prostate image shown in FIG. 3, in the case that a sixth probe is required for effective cryosurgical ablation of the prostate.
Figure 25:
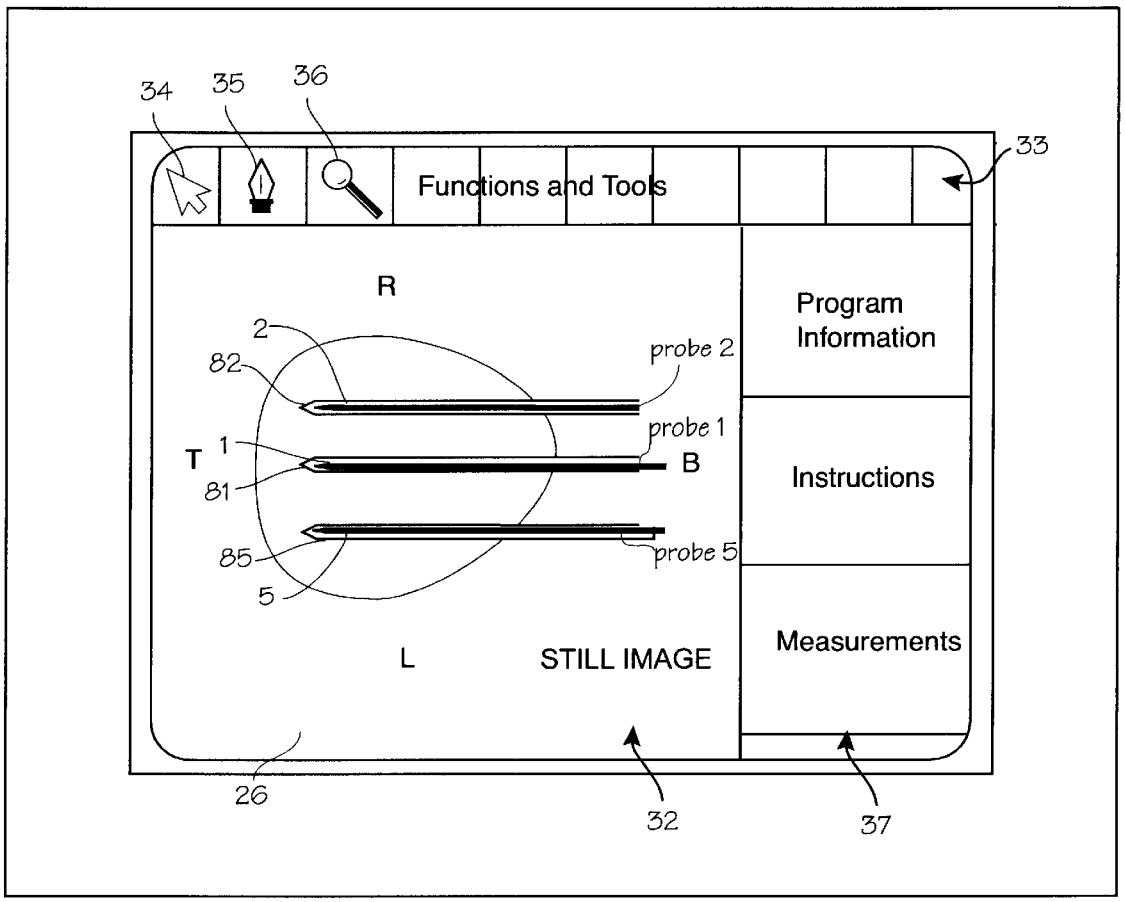
FIG. 25 is an illustration of the system output indicating the actual placement of cryoprobes in relation to the displayed optimum placement of cryoprobes within the prostate image shown in FIG. 2.

In a prostate where L1 is less that 35 mm across, only probe 5 is used, and it is located at or near the horizontal center of the prostate outline. As illustrated in FIG. 21, the system sets iY5 at bottom of outline. The system also defines the horizontal line 1/3 the way down H1 from the urethra to rectum (the horizontal line labeled as pctUrethra+1/3), and defines the horizontal line 18 mm above iY5 (the horizontal line labeled iY5−18). The system then selects the lowest of these two lines as the vertical position for probe 5. Probe 5 is placed horizontally on the horizontal midpoint between probes 1 and 4 (expected to be on or near H1). Thus, as an alternate to placement of both probes 5 and 6, the system places probe 5, based upon the width of the prostate, in the center portion of the prostate at the posterior-most location of (1) 1/3 the distance posterior from the urethra to the rectum or (2) 18 mm anterior to the posterior extremity of the prostate After calculation of the optimal placement of the cryoprobes according to either of the methods above, the system graphically displays the desired locations to assist the operator in placing the actual probes in the prostate of the patient. The optimal location of the probes is indicated in the horizontal cross section by a graphic representation overlaid over the live ultrasound images of FIGS. 3 and 2 and/or the still images of FIGS. 6 and 4. The desired representation is illustrated in FIGS. 22 and 25. FIG. 22 is an illustration of the system output indicating the optimum placement of cryoprobes within the prostate horizontal cross sectional image shown in FIG. 2. The suggested probe placement is indicated by graphical markers 75, 76, 77, 78, 79 and 80 for Probes 1, 2, 3 4, 5 and 6 respectively. The markers are placed in the display by the computer system, overlaying the ultrasound image of the prostate horizontal cross section.

Figure 23:
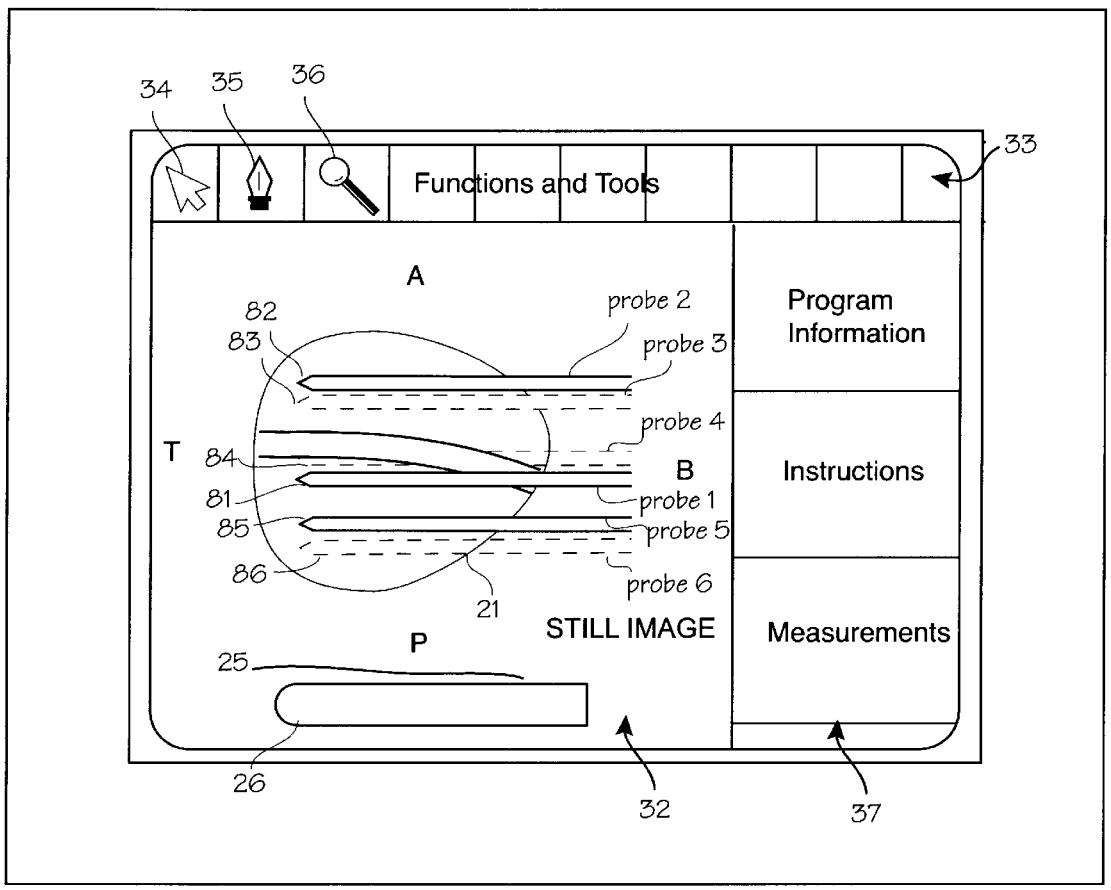
FIG. 23 is an illustration of the system output indicating the optimum placement of cryoprobes within the prostate image shown in FIG. 2.
Figure 24:
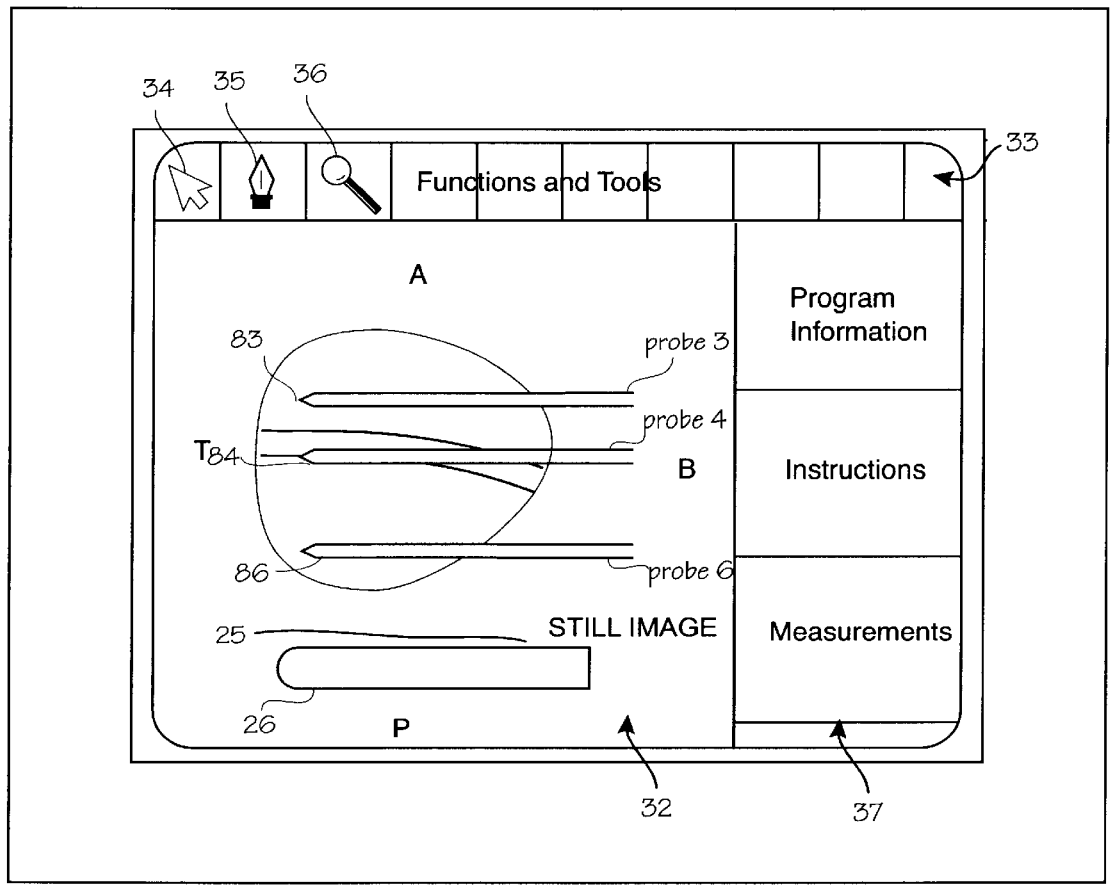
FIG. 24 is an illustration of the system output indicating the optimum placement of cryoprobes within the prostate image shown in FIG. 2.

The system also provides an illustration of the placement of the probes in the sagittal cross section. FIGS. 23 and 24 show the display presented by the computer system of graphical markers for each probe. The vertical position of the probes is dependent on the positions calculated in reference to calculated positions in the horizontal cross section. FIGS. 23 and 24 show the system output indicating the optimum placement of cryoprobes within the prostate longitudinal cross sectional image shown in FIG. 3. The suggested probe placement, as viewed on the sagittal plane, is indicated by graphical markers, 81, 82, 83, 84, 85 and 86. The markers are placed in the display by the computer system, overlaying the ultrasound image of the prostate sagittal cross section. Since probes 2 and 3, and probes 1 and 4, and probes 5 and 6 are likely to be symmetrically located in reference to the line H1, the probes in these pairs will overlap in this view. Thus, probes 3, 4 and 6 are displayed as shown in FIG. 24. The computer system permits the operator to switch between views of FIG. 23 and FIG. 24. FIG. 23 is used by the operator to assist in placement of Probes 1, 2 and 5, while FIG. 24 is used to assist in placement of Probes 3, 4 and 6.

Figure 26:
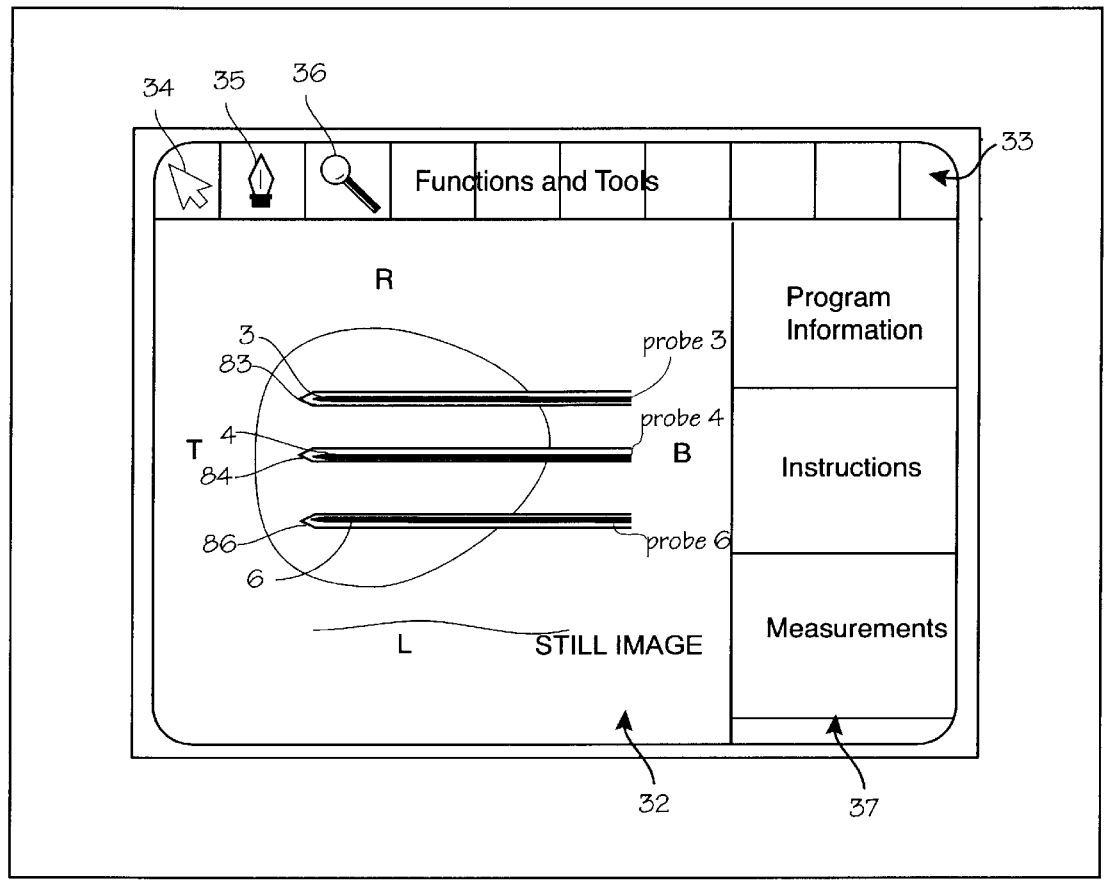
FIG. 26 is an illustration of the system output indicating the actual placement of cryoprobes in relation to the displayed optimum placement of cryoprobes within the prostate image shown in FIG. 2, displaying probes and graphical markers obscured in the view of FIG. 25.
Figure 27:
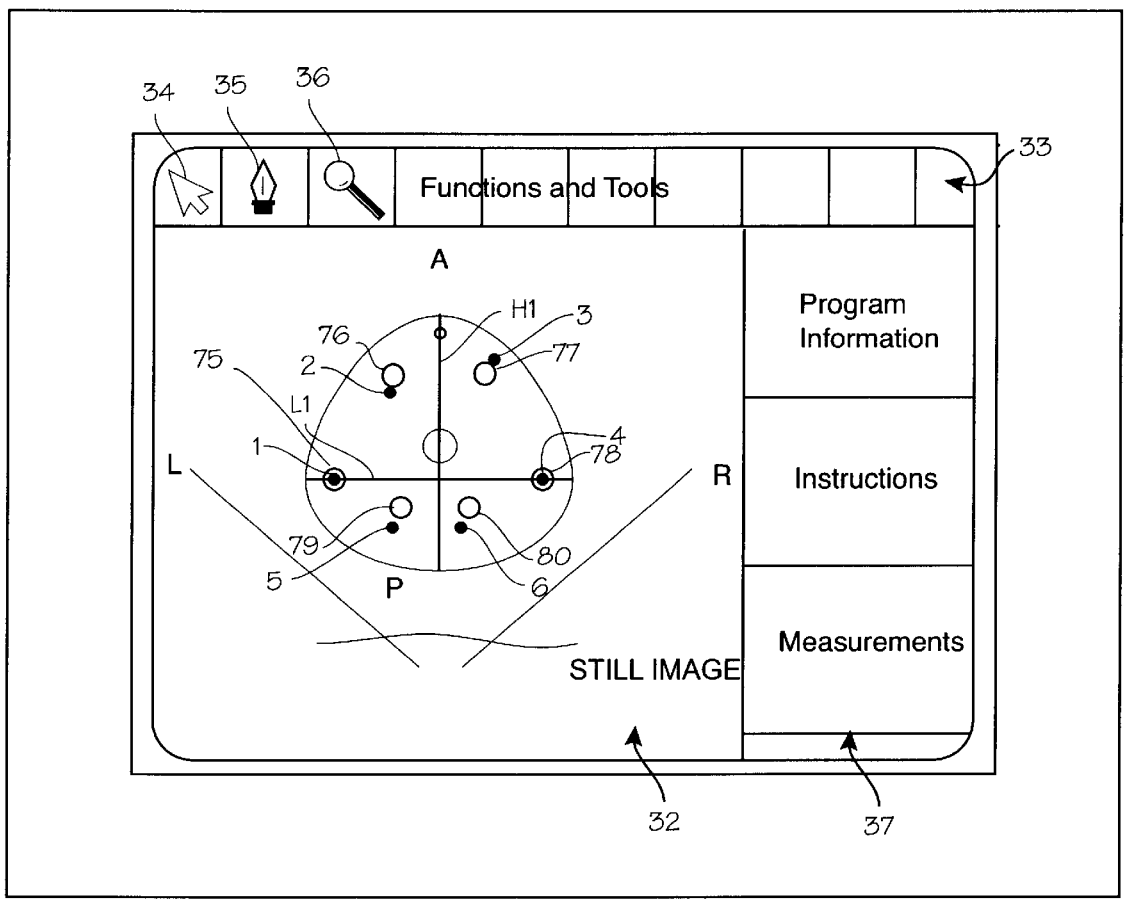
FIG. 27 is an illustration of the system output indicating the actual placement of cryoprobes in relation to the displayed optimum placement of cryoprobes within the prostate image shown in FIG. 3.

With the optimal probe placements calculated and graphical markers placed on the display, the operator may insert cryoprobes into the prostate. FIGS. 25, 26 and 27 illustrate the feedback provided to the operator indicating the actual position of the cryoprobes in relation to the suggested placement shown in FIGS. 22, 23 and 24. Referring to FIG. 27, the graphical markers 75, 76, 77, 78, and 80 are shown in the horizontal cross section, displayed as generated by the computer system. In addition, the ultrasound image of the probes is displayed in the display area, since the probes enter the ultrasound imaging field and are imaged by the ultrasound imaging system. As the surgeon inserts each probe into the prostate, its placement as indicated by the ultrasound system may be compared to the suggested probe placement, and the surgeon may manipulate the probes so that the ultrasound images of the actual probes align with the graphical markers. In FIG. 27, the exemplary placement of probes is illustrated. Probe 1 has been placed in good correspondence with the template provided by the computer, and the ultrasound image is aligned with the graphical marker 75. Probe 2 has been placed in a position different than its associated graphical marker 76, and the surgeon may decide on that basis to reinsert the probe to more closely align it with the marker. Probe 3 has been placed close to the marker 77, and the surgeon may decide to reposition the probe or to leave it in place. Likewise, Probes 4 and 5 appear in the display on or near their associated markers 78 and 80, providing feedback to the surgeon ensuring proper placement of the probes.

Referring to FIG. 25, the graphical markers 81, 82 and 85 are shown, displayed as generated by the computer system. In addition, the ultrasound image of the probes is displayed in the display area, since the probes enter the ultrasound imaging field and are imaged by the ultrasound imaging system. Again, the surgeon may view the ultrasound image of the actual probes, and place the probes as closely as possible positions corresponding to the markers. FIG. 26 shows a display containing the graphical markers 83 and 84 corresponding to probes 3 and 4 which are located on the right side of the prostate relative to the anterior/posterior centerline. These displays help the operator in placing the probes as desired in parallel relationship with the ultrasound probe and the rectal wall. The operator may switch repeatedly between the displays of FIGS. 25, 26 and 27 while inserting the cryoprobes, selectively displaying the image of the horizontal cross section and the image of the coronal cross section, to monitor the progress of the probes and ensure placement of the probes is accomplished in the positions suggested by the computer system. When cryoprobes placement is satisfactory, the surgeon will start the flow of cooling gas to freeze the prostate. The freezing operation can be confirmed in the ultrasound image by watching the iceballs (the mass of frozen tissue) around each cryoprobes form. The extent of the iceballs and the extent of the prostate that is frozen is monitored to ensure that substantially all of the prostate is frozen. The freezing process may be repeated to ensure ablation of the prostate.

The section of the computer program which performs these calculations is provided as FIG. 28, which is programmed in the C++ programming language. The program implements the second method described above in relation to FIGS. 14 through 22. The section of the code which finds the proper vertical location for probes 2 and 3 in the anterior lobe of the prostate starts at item number 90. The section of code which determines if the gland is too large or small is indicated by item number 91. The section of the code which finds the proper horizontal and vertical location for probes 2 and 3 in the anterior lobe of the prostate is labeled as item 92. The section of the program which calculates the position of probes 1 and 4 is indicated by item number 93. This segment of code also incorporates a test for adequate symmetry of the prostate, in that if probe 1 or probe 4 cannot be properly place, the system communicates this to the operator (leading to re-imaging or cancellation of the computer assisted surgery). The section of the program which calculates the position of probes 5 and 6 (or only probe 5) is indicated by item number 94.

Thus, we have described a system for assisting surgeons in performing cryosurgery of the prostate by calculating optimal positions for cryoprobes and providing display based templates for overlay over an ultrasound image display, and displaying actual cryoprobes ultrasound images together with template images so that the surgeon may compare suggested and actual placement of the probes, and adjust placement accordingly. The method and system is described above in relation to our CRYOcare™ cryosurgical system, which is provided with up to eight independently controlled 3 mm argon powered cryoprobes. The system cools the probes to cryosurgically effective temperatures (typically below −120° C.) through Joule-Thomson cooling within the probe tips. The system may be implemented with other cooling systems such as liquid nitrogen cryoprobes and mixed gas cryoprobes. The placement of probes is calculated based on this system, and the calculations may be adjusted for different systems and numbers of probes. Additionally, while the system has been described with ultrasound as the imaging mechanism and the rectum as the point of view, the system may be implemented with other imaging systems such as fluoroscopy or new imaging systems. The system may be adapted to other forms of ablation and treatment of the prostate or other organs, with adjustments in the calculations being made to account for the ablative range of the devices used and the geometry of the organ. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A method for assisting a surgeon in placing cryoprobes in the prostate of a human patient, wherein the cryoprobes are inserted through the skin of the perineal area of the patient and into the prostate, including the anterior lobe of the prostate and the posterior lobe of the prostate, said method comprising the steps of:

providing a first cryoprobe, a second cryoprobe, a third cryoprobe, a fourth cryoprobe, a fifth cryoprobe and a sixth cryoprobe, and a cooling system for cooling the cryoprobes to cryosurgically effective temperatures;

providing an ultrasound imaging system including a transrectal ultrasound probe and ultrasound display; said ultrasound imaging system being capable of creating a first image of the prostate on a first plane and a second image of the prostate in a second plane;

providing a computer system capable of accepting input from an operator identifying the outline of the prostate in reference to the first image and the second image of the prostate displayed by the ultrasound imaging system;

said computer system being programmed with software capable of performing the following steps;

computing an optimal position for placement of a first cryoprobe and second cryoprobe in the anterior lobe of the prostate gland;

computing an optimal position for placement of a third cryoprobe and fourth cryoprobe in the posterior lobe of the cryoprobe;

computing the need for the sixth cryoprobe, and upon determining the need for the sixth cryoprobe, computing an optimal position for placement of the fifth cryoprobe and the sixth cryoprobe in the posterior lobe of the prostate;

alternately, upon determining that a sixth cryoprobe is unnecessary, computing an optimal position for placement of the fifth cryoprobe in the posterior lobe of the prostate;

displaying a first set of graphical markers on the display of the first image at positions corresponding to the computed optimal positions for each of the first cryoprobe, the second cryoprobe, the third cryoprobe, the fourth cryoprobe, the fifth cryoprobe and the sixth cryoprobe;

displaying a second set of graphical markers on the display of the second image at positions corresponding to the computed optimal positions for each of the first cryoprobe, the second cryoprobe, the third cryoprobe, the fourth cryoprobe, the fifth cryoprobe and the sixth cryoprobe;

permitting the operator to selectively display the first image and the second image.

2. A method for assisting a surgeon in placing cryoprobes in the prostate of a human patient, wherein the cryoprobes are inserted through the skin of the perineal area of the patient and into the prostate, including the anterior lobe and the posterior lobe of the prostate, said system comprising a display for displaying an ultrasound image of the prostate, a template of suggested cryoprobes placements in the prostate, and images of cryoprobes placed within the prostate, and a computer system programmed to compute the position of the cryoprobes with a method comprising the steps of;

determining the width of the prostate based on the image, and determining the number of cryoprobes required based on the width of the prostate;

determining the position of two cryoprobes in the anterior lobe of the prostate based upon the width of the prostate approximately at the anterior-most location of (1) 16 mm posterior to the anterior extremity of the prostate, (2) 4 mm anterior to the center of the prostatic urethra, or (3) $7/16$ of the total thickness of the prostate from the anterior extremity of the prostate;

determining the position of two cryoprobes in the posterior lobe of the prostate based upon the width of the prostate at the anterior-most location of (1) approximately $5/8$ of the total thickness of the prostate from the anterior extremity of the prostate or (2) 16 mm posterior to the two cryoprobes positioned in the anterior lobe of the prostate;

determining the position of two cryoprobes in the center portion of the posterior lobe of the prostate based upon the width of the prostate at a the anterior-most location of (1) approximately $1/4$ of the distance on the display from the rectum to the top of the display or (2) 16 mm posterior to the two cryoprobes positioned in the posterior lobe of the prostate;

alternately, based upon the width of the prostate, placing a single cryoprobes in the center portion of the prostate at the posterior-most location of (1) $1/3$ the distance posterior from the urethra to the rectum or (2) 18 mm anterior to the posterior extremity of the prostate;

wherein the positions determined by the computer system are displayed as graphical markers displayed with the ultrasound image of the prostate, and ultrasound images of cryoprobes are displayed with the ultrasound image of the prostate, thereby allowing the surgeon to compare actual cryoprobes placement with optimal cryoprobes placement as determined by the computer system.

3. A system for assisting a surgeon in placing a surgical instrument in an organ of a human patient through a placement point, said system comprising:

imaging means being capable of creating two-dimensional images of the organ on a plurality of planes; and creating images of the surgical instrument in place within the organ; and a template superimposed over the images of the organ, said template having a marker for pinpointing the desired placement point of the surgical instrument in the organ;

wherein the two-dimensional images of the organ, the surgical instrument displayed, and the marker are displayed as a two-dimensional representation to allow the surgeon to compare actual instrument placement with desired instrument placement.

4. The system of claim 3, wherein the imaging means is an ultrasound imaging system including an ultrasound transducer and ultrasound display.

5. The system of claim 3 wherein the template and marker are created by a computer system coupled to the imaging means.

6. The system of claim 3 wherein the template and marker are created by the surgeon.

7. A computer system having a display for assisting a surgeon place cryoprobes in the prostate of a human patient, wherein the cryoprobes are inserted though the skin of the perineal area of the patient and into the prostate, including the anterior lobe of the prostate and the posterior lobe of the prostate, the display adapted to display images of the prostate, said computer system being programmed with software capable of performing the following steps;

computing an optimal position for placement of a first cryoprobes and second cryoprobes in the anterior lobe of the prostate;

computing an optimal position for placement of a third cryoprobes and fourth cryoprobes in the posterior lobe of the cryoprobes;

computing the need for the sixth cryoprobes, and upon determining the need for the sixth cryoprobes, computing an optimal position for placement of the fifth cryoprobes and the sixth cryoprobes in the posterior lobe of the prostate;

alternately, upon determining that a sixth cryoprobes is unnecessary, computing an optimal position for placement of the fifth cryoprobes in the posterior lobe of the prostate;

displaying a first set of graphical markers on the display at positions corresponding to the computed optimal positions for each of the first cryoprobes, the second cryoprobes, the third cryoprobes, the fourth cryoprobes, the fifth cryoprobes and the sixth cryoprobes.

8. A system for assisting a surgeon in placing a plurality of cryoprobes in the prostate of a human patient, wherein the cryoprobes are inserted through the skin of the perineal area of the patient and into the prostate, including the anterior lobe of the prostate and the posterior lobe of the prostate, said system comprising:

an ultrasound imaging system including a transrectal ultrasound probe and ultrasound display; said ultrasound imaging system being capable of creating images of the prostate on a plurality of planes and said ultrasound imaging system being capable of creating images of the cryoprobes;

a computer system capable of accepting input from an operator identifying the outline of the prostate in reference to the image of the prostate displayed by the ultrasound imaging system;

said computer system being programmed with software capable of performing the following steps;
      computing an optimal number of cryoprobes;
      computing optimal positions for placement cryoprobes of said cryoprobes in the prostate;
      displaying graphical markers on the display at positions corresponding to the computed optimal positions for each of the cryoprobes;
      permitting the operator to selectively display from the plurality of planes.

9. A system for assisting a surgeon in placing cryoprobes in the prostate of a human patient, wherein the cryoprobes are inserted through the skin of the perineal area of the patient and into the prostate, including the anterior lobe of the prostate and the posterior lobe of the prostate, said system comprising:

an ultrasound imaging system being capable of creating images of the prostate on a plurality of planes and creating images of the cryoprobes;

a template having markers corresponding to the desired placement of each cryoprobes in the prostate; and a display adapted to display the images of the prostate and the images of the cryoprobes; and display the template and the markers superimposed over the images of the prostate and the images of the cryoprobes.

10. The system of claim 9 wherein the template and markers are created by a computer system coupled to the ultrasound imaging system.

11. The system of claim 9 wherein the template and markers are created by the surgeon.

* * * * *